United States Patent
Reinhardt et al.

(10) Patent No.: US 12,053,533 B2
(45) Date of Patent: Aug. 6, 2024

(54) FLUORESCENT PROBE FOR CYCLOOXYGENASE-2

(71) Applicant: The Board of Trustees of the University of Illinois, Urbana, IL (US)

(72) Inventors: Christopher J. Reinhardt, Urbana, IL (US); Anuj K. Yadav, Champaign, IL (US); Jefferson Chan, Savoy, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 417 days.

(21) Appl. No.: 17/240,427

(22) Filed: Apr. 26, 2021

(65) Prior Publication Data
US 2021/0330822 A1 Oct. 28, 2021

Related U.S. Application Data

(60) Provisional application No. 63/015,164, filed on Apr. 24, 2020.

(51) Int. Cl.
*A61K 51/04* (2006.01)
*C07D 311/72* (2006.01)

(52) U.S. Cl.
CPC ........ *A61K 51/0474* (2013.01); *C07D 311/72* (2013.01)

(58) Field of Classification Search
CPC .... A61K 51/00; A61K 51/04; A61K 51/0474; C07D 311/72; C09B 19/00; G01N 33/582
USPC .......................... 424/1.11, 1.65, 9.1, 9.2, 9.6
See application file for complete search history.

(56) References Cited

U.S. PATENT DOCUMENTS

| | | | | |
|---|---|---|---|---|
| 7,432,372 B2 * | 10/2008 | Batchelor | ............ | C07D 495/04 544/99 |
| 8,192,948 B1 | 6/2012 | Feather-Henigan | | |
| 9,212,385 B2 | 12/2015 | Batchelor et al. | | |
| 2009/0252678 A1 | 10/2009 | Marnett et al. | | |

OTHER PUBLICATIONS

Cayman Chemical, Product Information, ADHP, Item No. 10010469, 1 page (Year: 2023).*
Siewiera et al., Diagnostyka Laboratoryjna, vol. 48, No. 2, pp. 153-162 (Year: 2012).*
Yadav et al, Angew. Chem. Int. Ed., vol. 59, pp. 3307-3314 (Year: 2020).*
Gorris et al., "Mechanistic Aspects of Horseradish Peroxidase Elucidated Through Single-Molecule Studies," J Am Chem Soc., 131(17):6277-6282, May 2009.
Gumiero et al., "Nature of the Ferryl Heme in Compounds I and II," J Biol Chem., 286(2):1260-1268, Jan. 2011.
Kalgutkar et al., "Biochemically Based Design of Cyclooxygenase-2 (COX-2) Inhibitors: Facile Conversion of Nonsteroidal Antiinflammatory Drugs to Potent and Highly Selective COX-2 Inhibitors," Proc Natl Acad Sci U S A., 97(2):925-930, Jan. 2000.
Kulmacz et al., "Comparison of the Properties of Prostaglandin H Synthase-1 and -2," Prog Lipid Res., 42(5):377-404, Sep. 2003.
Rouzer et al., "Cyclooxygenases: Structural and Functional Insights," J Lipid Res., 50:Suppl:S29-34, Apr. 2009.
Uddin et al., "Selective Visualization of Cyclooxygenase-2 in Inflammation and Cancer by Targeted Fluorescent Imaging Agents," Cancer Res., 70(9):3618-3627, May 2010.
Yadav et al., "An Activity-Based Sensing Approach for the Detection of Cyclooxygenase-2 in Live Cells," Angew Chem Int Ed Engl., 59(8):3307-3314, Feb. 2020.
Yadav et al., "An Activity-Based Sensing Approach for the Detection of Cyclooxygenase-2 in Live Cells," Angew Chem Int Ed Engl., 59(8):3307-3314, Feb. 2020, Supporting Information.
Zhang et al., "An Off-On COX-2-Specific Fluorescent Probe: Targeting the Golgi Apparatus of Cancer Cells," J. Am. Chem. Soc., 135(31):1663-11669, Jul. 2013.

* cited by examiner

*Primary Examiner* — D. L. Jones
(74) *Attorney, Agent, or Firm* — Haukaas Fortius PLLC; Michael Haukaas

(57) ABSTRACT

Cyclooxygenase-2 (COX-2) over-expression is prominent in inflammatory diseases, neurodegenerative disorders, and cancer. Directly monitoring COX-2 activity within its native environment poses an exciting approach to account for and illuminate the effect of the local environments on protein activity. Herein, we report the development of CoxFluor, the first activity-based sensing approach for monitoring COX-2 within live cells with confocal microscopy and flow cytometry. CoxFluor strategically links a natural substrate with a dye precursor to engage both the cyclooxygenase and peroxidase activities of COX-2. This catalyzes the release of resorufin and the natural product, as supported by molecular dynamics and ensemble docking. CoxFluor enabled the detection of oxygen-dependent changes in COX-2 activity that are independent of protein expression within live macrophage cells.

16 Claims, 15 Drawing Sheets

FLUORESCENT PROBE FOR CYCLOOXYGENASE-2

RELATED APPLICATIONS

This application claims priority under 35 U.S.C. § 119(e) to U.S. Provisional Patent Application No. 63/015,164, filed Apr. 24, 2020, which is incorporated herein by reference.

BACKGROUND OF THE INVENTION

Cyclooxygenase (COX, E.C. 1.14.99.1) is the key biosynthetic enzyme that initiates the synthesis of prostaglandins from their linear lipid precursor, arachidonic acid (AA). After production, the prostaglandins function as important lipid-based mediators that regulate physiological processes, such as gastric epithelial protection, hemostasis, and sodium metabolism. At higher concentrations the prostaglandins act as potent pro-inflammatory compounds through IL-6 expression. These prostaglandins can be further elaborated by a variety of tissue-specific isomerases and synthases to afford the entire gambit of prostanoids (AA-derived prostaglandins). Due to its critical role in prostaglandin synthesis and the immune response, COX over-expression has been identified as a prominent phenotype in inflammation, neurodegenerative disorders, and cancer.

Two isoforms of human COX have been identified (COX-1 and -2), which both catalyze the rate-limiting production of prostaglandin H2 ($PGH_2$). The major distinctions between COX-1 and COX-2 are their expression profile: COX-1 is constitutively expressed in most cell types whereas COX-2 expression is typically induced by inflammatory and proliferative conditions for rapid prostaglandin production. Under pathological states COX-2 is typically over-expressed resulting in both acute and chronic inflammatory conditions. For example, COX-2 is over-expressed in a significant number of rodent and human tumors and COX-2 and inducible nitric oxide synthase expression levels correlate with poor clinical outcomes due to increased angiogenesis, proliferation, and migration. Moreover, COX-2 has been identified as the key enzyme responsible for arachidonyl ethanolamine's cancer specific toxicity through the bio-synthesis of J-series prostaglandins.

As an important target of both biological and pharmaceutical studies, there is a clear need for tools capable of measuring COX-2 activity within its native environment. To date, there are a limited number of strategies for detecting the presence, but not activity, of COX-2 in living systems. For example, selective inhibitors of COX-2 have been radio-labeled ($^{18}F$, $^{123}I$, $^{125}I$, $^{11}C$) or appended to dyes for PET/SPECT or fluorescence imaging, respectively. These imaging agents report on relative COX-2 expression profiles; however, they remain in a constant 'on' state, regardless of if it is bound to COX-2, leading to higher background or requiring washing steps. This led to the development of activatable fluorescent inhibitors that afford an "off-on" response upon binding. This class of sensor is designed to fold into a conformation that facilitates fluorescence attenuation via intramolecular #-stacking. Upon protein binding, the COX-2 inhibitor is sequestered away from the fluorophore and the protein-small-molecule adduct is rendered fluorescent. Despite this notable improvement, 'off-on' fluorescent inhibitors only report on whether COX-2 is present, but not if the enzyme is catalytically active. A variety of factors beyond enzyme concentration can affect the activity of COX-2 in a cellular environment including temperature, pH, substrate concentrations (peroxides, AA and/or molecular oxygen), and post-translational modifications (oligosaccharides). For example, COX-2 functions as a conformational heterodimer where binding of substrate or other fatty acids allosterically regulate the enzyme activity.

Current cell-compatible technologies can only detect the presence of COX-2, but not the activity where the activity can be affected by temperature, pH, substrate concentrations, and post-translational modifications. Accordingly, new technologies are needed which can directly report on COX-2 activity with minimal cross-reactivity from similar enzymes and allow for live-cell analysis of COX-2 activity.

SUMMARY

To address these limitations, we developed CoxFluor, the first isoform-selective, activity-based fluorescence probe for COX-2. CoxFluor proved to be selective for COX-2 over a panel of other biologically relevant enzymes (including COX-1), enabled validation of COX-2 inhibitors within in vitro assays, and was successfully applied for the live-cell imaging of basal COX-2 activity. This work provides important insights into the development of COX-2 selective probes and outlines the utility of CoxFluor for evaluating enzyme activity both in vitro and within live-cell models.

Accordingly, this disclosure provides a compound of Formula I:

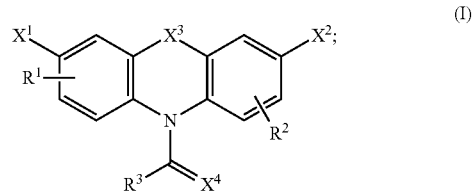

wherein
- $X^1$ and $X^2$ are independently OH, SH, or OC(=O)($C_1$-$C_6$)alkyl;
- $X^3$ is O, S, $SiR_2$, $SiPhs$, $CR_2$, $CPh_2$, C(fluorene), C(=O), C(=S), P(=O)R, or P(=O)OR wherein R is —($C_1$-$C_6$)alkyl;
- $X^4$ is O or S;
- $R^1$ and $R^2$ are independently H, halo, amino, nitro, cyano, or —($C_1$-$C_6$)alkyl; and
- $R^3$ is the alkyl moiety of arachidonic acid wherein the alkyl moiety is unsaturated or saturated; or
- $R^3$ is the alkyl moiety of a prostaglandin wherein the alkyl moiety is substituted with heteroatoms.

This disclosure also provides a method for imaging cyclooxygenase-2 (COX-2) activity comprising:
a) contacting a substrate and a compound of Formula IIB:

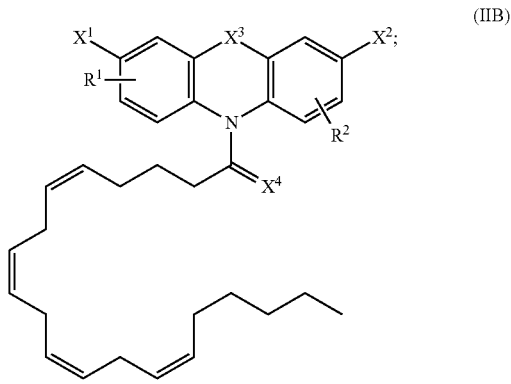

wherein
- $X^1$ and $X^2$ are independently OH, SH, or OC(=O)($C_1$-$C_6$)alkyl;
- $X^3$ is O, S, $SiR_2$, $SiPhs$, $CR_2$, $CPh_2$, C(fluorene), C(=O), C(=S), P(=O)R, or P(=O)OR wherein R is —($C_1$-$C_6$)alkyl;
- $X^4$ is O or S; and
- $R^1$ and $R^2$ are independently H, halo, amino, nitro, cyano, or —($C_1$-$C_6$)alkyl; and b) quantifying the fluorescent intensity of the contacted substrate by comparing the fluorescent intensity of the contacted substrate to a control;
thereby imaging the COX-2 activity of the substrate.

The invention provides novel compounds of Formula I, Formula II/IIB, and Formula III, intermediates for the synthesis of compounds of Formula I, Formula II/IIB, and Formula III, as well as methods of preparing compounds of Formula I, Formula II/IIB, and Formula III. The invention also provides compounds of Formula I, Formula II/IIB, and Formula III that are useful as intermediates for the synthesis of other useful compounds. The invention provides for the use of compounds of Formula I, Formula II/IIB, and Formula III for the manufacture of imaging probes for the detection of enzymatic activity, such as COX-2.

The invention provides for the use of the compositions described herein for use in medical diagnosis. The medical diagnosis can be for cancer, inflammatory responses, and neurodegenerative disorders. The invention also provides for the use of a composition as described herein for the identification and characterization of a medicament to treat a disease in a mammal, for example, cancer in a human. The composition can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
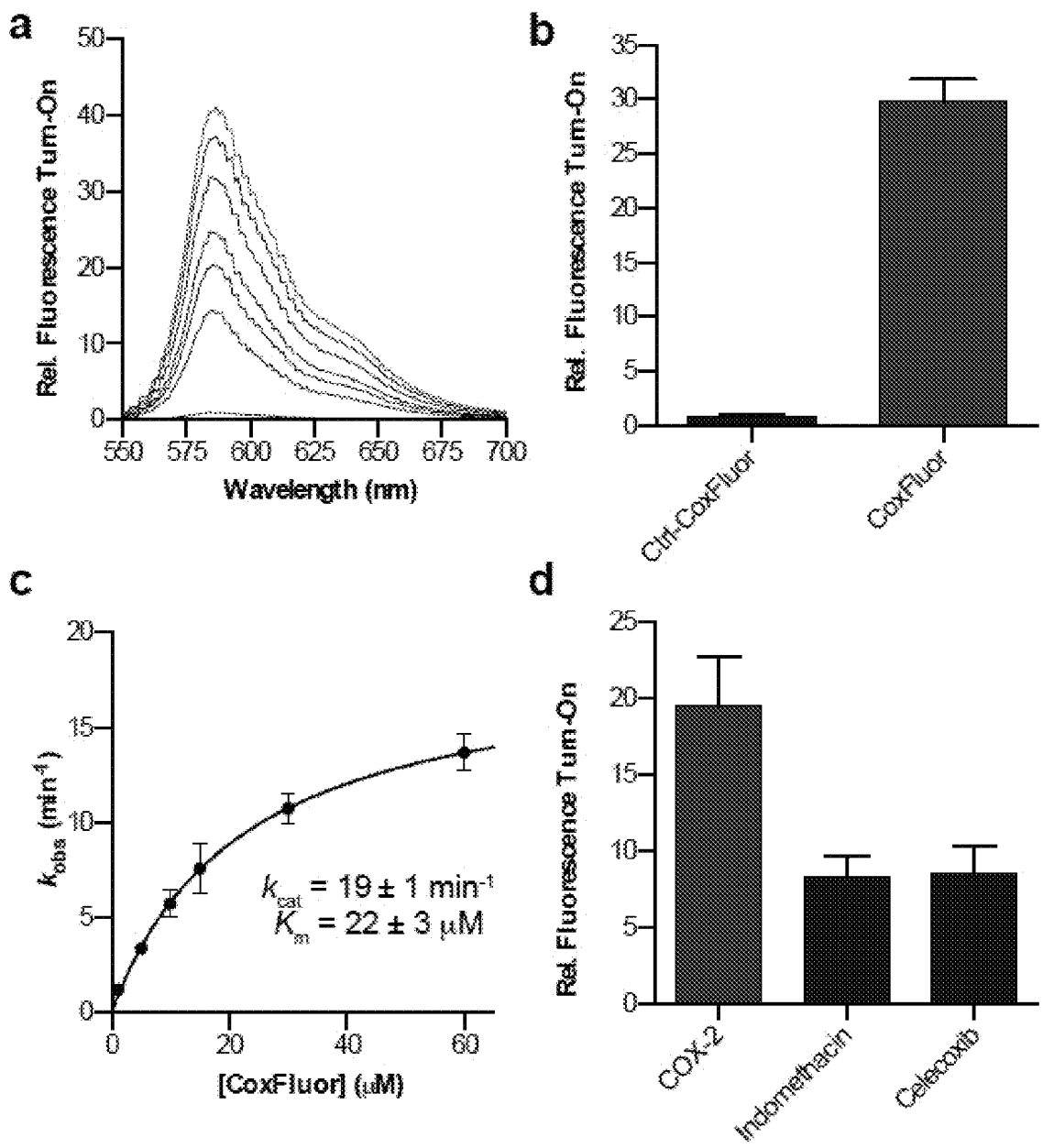
FIG. 1. (a) Relative fluorescence for CoxFluor (10 μM) incubated with COX-2 (250 nM) and hemin (1 μM) over the course of 4 h. (b) Relative fluorescent intensity of CoxFluor and Ctrl-CoxFluor after incubation with COX-2 (250 nM) and hemin (1 μM) for 4 h. (c) Michaelis-Menten kinetics for COX-2-catalyzed (50 nM) release of resorufin in the presence of hemin (200 nM). (d) Inhibition of COX-2 (250 nM) and hemin (1 μM) by indomethacin (10 μM) and celecoxib (10 μM). All experiments were conducted at room temperature in 100 mM Tris HCl buffer (pH 8.0) and are reported as the mean±standard deviation (n=3) for parts b and d or the error from fitting for part c. Parts a/c and b/d were performed according to the fluorimeter and plate reader assays, respectively.

The over-expression of cyclooxygenase-2 (COX-2) is prominent in inflammatory diseases, neurodegenerative disorders, and cancer. Fluorescent dyes conjugated to COX-2 inhibitors have been employed to image COX-2 protein levels in living systems, however, these imaging agents can potentially perturb natural processes through protein inhibition, and they lack the ability to report on the activity of the enzyme, which is influenced by factors beyond enzyme concentration. In this study, we have developed CoxFluor, the first activity-based fluorescent probe selective for COX-2. The probe works by initially serving as a substrate for cyclooxygenase activity, followed by release of the fluorophore via the enzyme's native peroxidase active site.

CoxFluor features a non-fluorescent resorufin dye precursor appended to arachidonic acid, the natural COX substrate, through an amide linkage. Owing to the bulky nature of the dye precursor, cross-reactivity with COX-1 was not observed. In contrast, incubation of CoxFluor with COX-2 resulted in probe activation and a concomitant 41-fold fluorescent turn-on response. Molecular dynamic simulations and ensemble docking support a two-step mechanism for turnover including dioxygenation by the cyclooxygenase active site, followed by peroxidase oxidation to cleave the sessile amide bond. CoxFluor was successfully employed to image or detect COX-2 activity in HEK293T and RAW macrophage cells.

This technology overcomes key drawbacks within the field where it can directly report on COX-2 activity with minimal cross-reactivity from similar enzymes. This advantage allows our technology to be employed for live-cell imaging or flow cytometric analysis of COX-2 activity, where existing, commercially available kits cannot be used. This is important because the current technologies can only detect the presence of COX-2, but not the activity where the activity can be affected by temperature, pH, substrate concentrations, and post-translational modifications.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983); for heterocyclic synthesis see Hermanson, Greg T., Bioconjugate Techniques, Third Edition, Academic Press, 2013.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group optionally includes a carbon chain moiety that is an alkenyl or alkynyl group. The alkyl can be a monovalent hydrocarbon radical, as described and exemplified above, or it can be a divalent hydrocarbon radical (i.e., an alkylene).

An alkylene is an alkyl group having two free valences at a carbon atom or two different carbon atoms. Similarly, alkenylene and alkynylene are respectively an alkene and an alkyne having two free valences at two different carbon atoms.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof, such as racemic mixtures, which form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

Embodiments of the Invention

This disclosure provides a compound of Formula I:

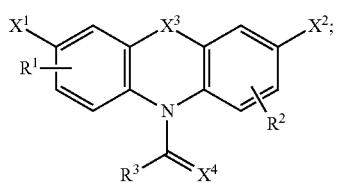

wherein
$X^1$ and $X^2$ are independently OH, SH, or OC(=O)($C_1$-$C_6$)alkyl;
$X^3$ is O, S, $SiR_2$, SiPhs, $CR_2$, $CPh_2$, C(fluorene), C(=O), C(=S), P(=O)R, or P(=O)OR wherein R is —($C_1$-$C_6$)alkyl;
$X^4$ is O or S;
$R^1$ and $R^2$ are independently H, halo, amino, nitro, cyano, or —($C_1$-$C_6$)alkyl; and
$R^3$ is the alkyl moiety of arachidonic acid wherein the alkyl moiety is unsaturated or saturated; or
$R^3$ is the alkyl moiety of a prostaglandin wherein the alkyl moiety is substituted with heteroatoms, or the alkyl moiety comprises heteroatom substitutions.

In some embodiments, $X^3$ is O, S, $Si(CH_3)_2$, SiPhs, $C(CH_3)_2$, $CPh_2$, C(fluorene), C(=O), C(=S), P(=O)R, or P(=O)OR wherein R is —($C_1$-$C_6$)alkyl. In some embodiments, the alkyl moiety of arachidonic acid is fully saturated, has one double bond, two double bonds, or three or more double bonds. In some other embodiments, the alkyl moiety of the prostaglandin is substituted with one or more oxygen atoms. In other embodiments, said oxygen atoms form hydroxyl groups, carboxylic acid groups, keto groups, ether groups, peroxy or peroxyl groups, or a combination thereof. In further embodiments, $R^3$ comprises the alkyl moiety of a prostanoid, such as $PGA_2$, $PGB_2$, $PGD_2$, $PGE_2$, $FGF_2$, $PGG_2$, $PGI_2$, $PGH_2$, $PGJ_2$, and the like.

In some embodiments, the compound is a compound of Formula II:

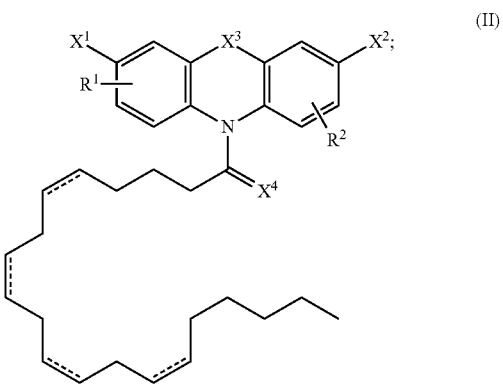

wherein each ------- is independently a double bond or a single bond.

In various embodiments, each ------- is a double bond. In other embodiments, the compound is a selective substrate for cyclooxygenase-2 (COX-2) over other enzymes. In yet other embodiments, each ------- is a single bond. In additional embodiments, the compound is not fluorescent or emits less fluorescence than Resorufin.

In various other embodiments, the compound is a compound of Formula III:

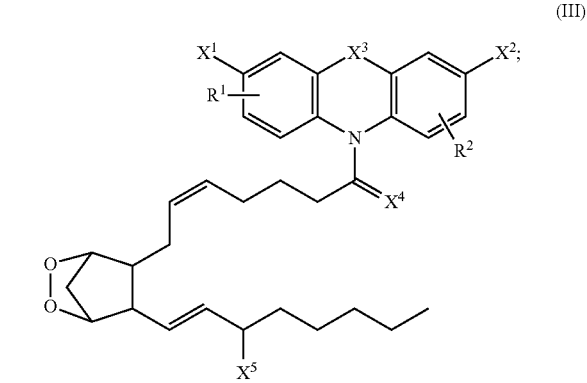

wherein $X^5$ is OH, SH, or OOH.

In various additional embodiments, $X^1$ and $X^2$ are OH, and $X^3$ and $X^4$ are O. In other embodiments, $R^1$ and $R^2$ are H. In some other embodiments, $X^4$ is O. In additional embodiments, the amide bond (e.g., C—N) is cleavable selectively over other enzymes at heme B (hemin, compound I, or compound II; see Scheme 1b) of the native COX-2 peroxidase active site. In some embodiments the oxidant is compound I (a radical cation), in other the oxidant is compound II (a neutral species).

In some additional embodiments, the compound is:

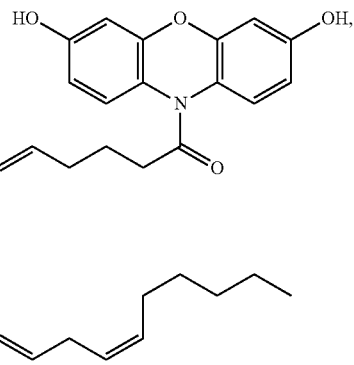

(CoxFluor)

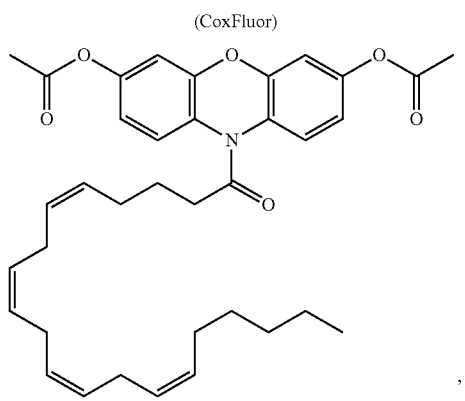

,

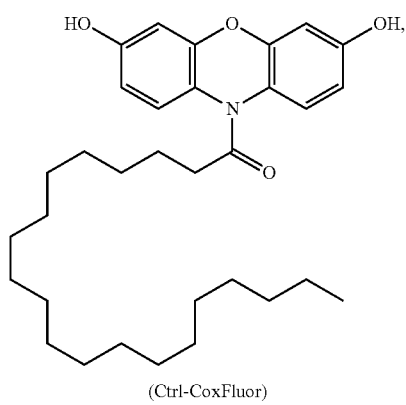

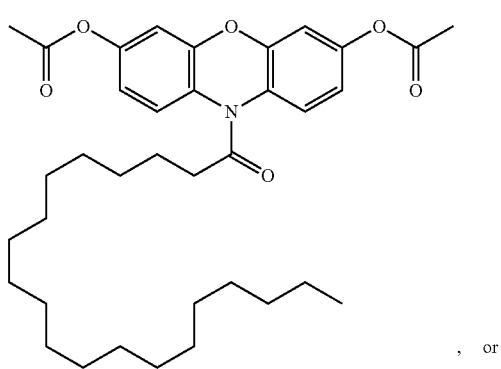

, or

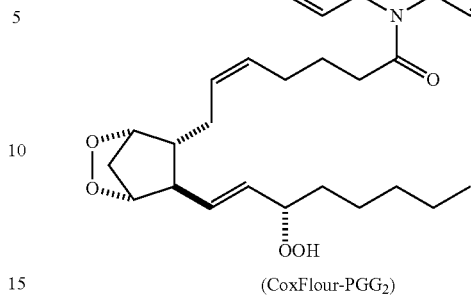

(CoxFlour-PGG$_2$)

In yet other embodiments, the compound is CoxFluor. In other embodiments, the compound is Ctrl-CoxFluor. In further embodiments, the compound has a quantum yield of about 0.29 and a molar extinction coefficient of about 820 $M^{-1}cm^{-1}$ at 572 nm.

Also, this disclosure provides a method for imaging cyclooxygenase-2 (COX-2) activity comprising:

a) contacting a substrate and a compound of Formula IIB:

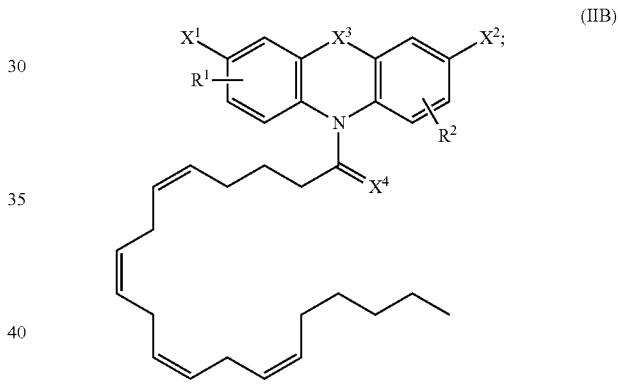

(IIB)

wherein $X^1$ and $X^2$ are independently OH, SH, or OC(=O)($C_1$-$C_6$)alkyl;

$X^3$ is O, S, $SiR_2$, $SiPhs$, $CR_2$, $CPh_2$, C(fluorene), C(=O), C(=S), P(=O)R, or P(=O)OR wherein R is —($C_1$-$C_6$)alkyl;

$X^4$ is O or S; and $R^1$ and $R^2$ are independently H, halo, amino, nitro, cyano, or —($C_1$-$C_6$)alkyl; and b) quantifying the fluorescent intensity of the contacted substrate by comparing the fluorescent intensity of the contacted substrate to a control;

thereby imaging the COX-2 activity of the substrate.

In various other embodiments, the substrate is COX-2 or a cell. In additional embodiments, the substrate is contacted with a second agent prior to step a). In yet other embodiments, the second agent depletes glutathione. In other additional embodiments, the substrate and the compound are contacted with a second agent at step a). In some embodiments, the second agent is a cyclooxygenase inhibitor or glutathione.

Additionally, this disclosure provides a probe compound comprising (or consisting of) a fluorescent compound conjugated to arachidonic acid or a prostaglandin via an amide bond wherein the C—N moiety of the amide bond enzymatically cleavable, and the fluorescent compound is less fluorescent when conjugated to arachidonic acid or a prostaglandin compared to the corresponding unconjugated fluorescent compound.

In various embodiments the fluorescent compound is Resorufin. In other embodiments, the fluorescent compound, for example Resorufin, is conjugated to an eicosanoid. In other embodiments, the eicosanoid is a thromboxane, leukotriene, lipoxin, resolvin, or eoxin.

Results and Discussion

Activity-based sensing of COX-2: An isoform-selective fluorogenic probe reports on enzymatic activity within live cells. A two-step activation facilitates the release of the natural product and resorufin for confocal imaging and flow cytometry. CoxFluor indicates that COX-2 activity can be regulated by oxygen without a change in the protein expression level.

Design and Synthesis. The design for CoxFluor consisted of 3,7-dihydroxyphenoxazine (reduced form of resorufin) linked to AA by a cleavable amide bond. We hypothesized that the lipid tail of CoxFluor could serve as a substrate for COX-2 in a manner similar to the natural substrate (Scheme 1a). After binding within the cyclooxygenase active site, the probe could undergo hydrogen atom extraction by the enzyme's Tyr385, followed by dioxygenation and cyclization to afford the CoxFluor-PGG$_2$ intermediate. After translocation to the peroxidase active site, the intermediate could intercept Compound I or Compound II for oxidation, generating an unstable oxygen-centered resorufin radical, followed by dismutation, and amide hydrolysis to release the fluorescent product and either PGG$_2$ or PGH$_2$ (after reduction, Scheme 1b).

Scheme 1

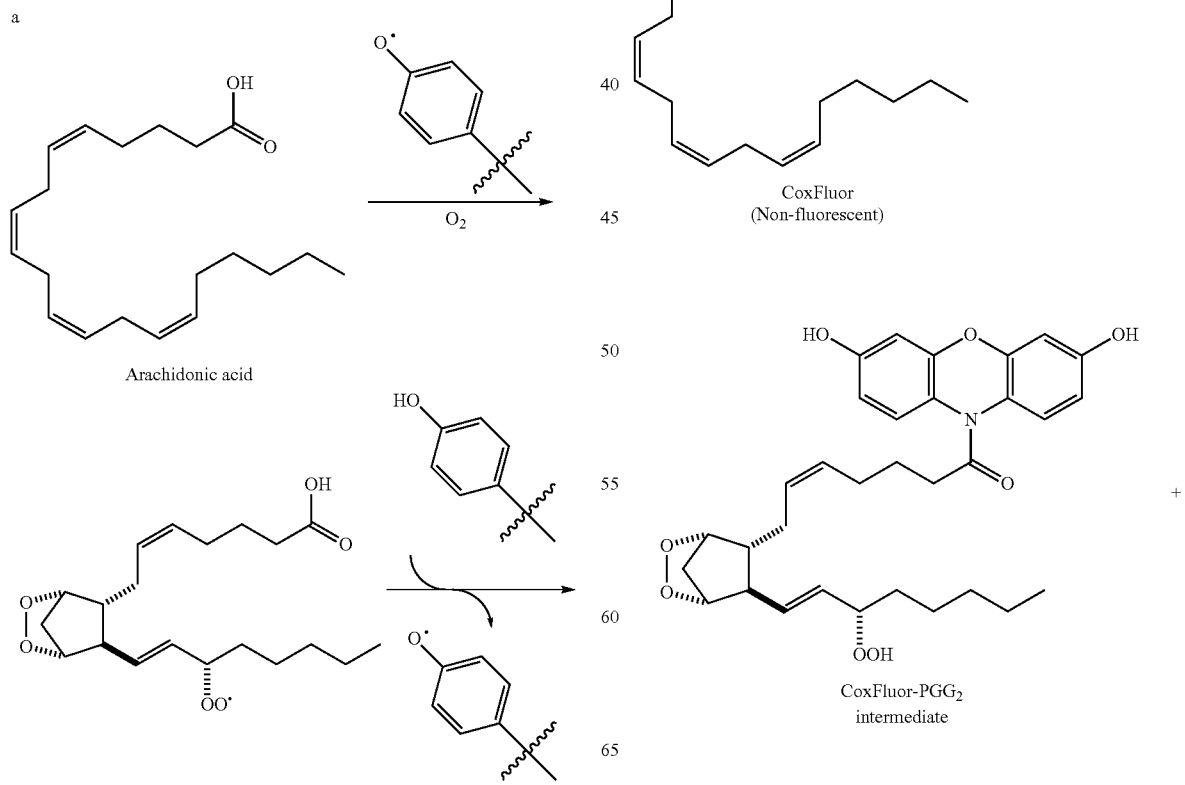

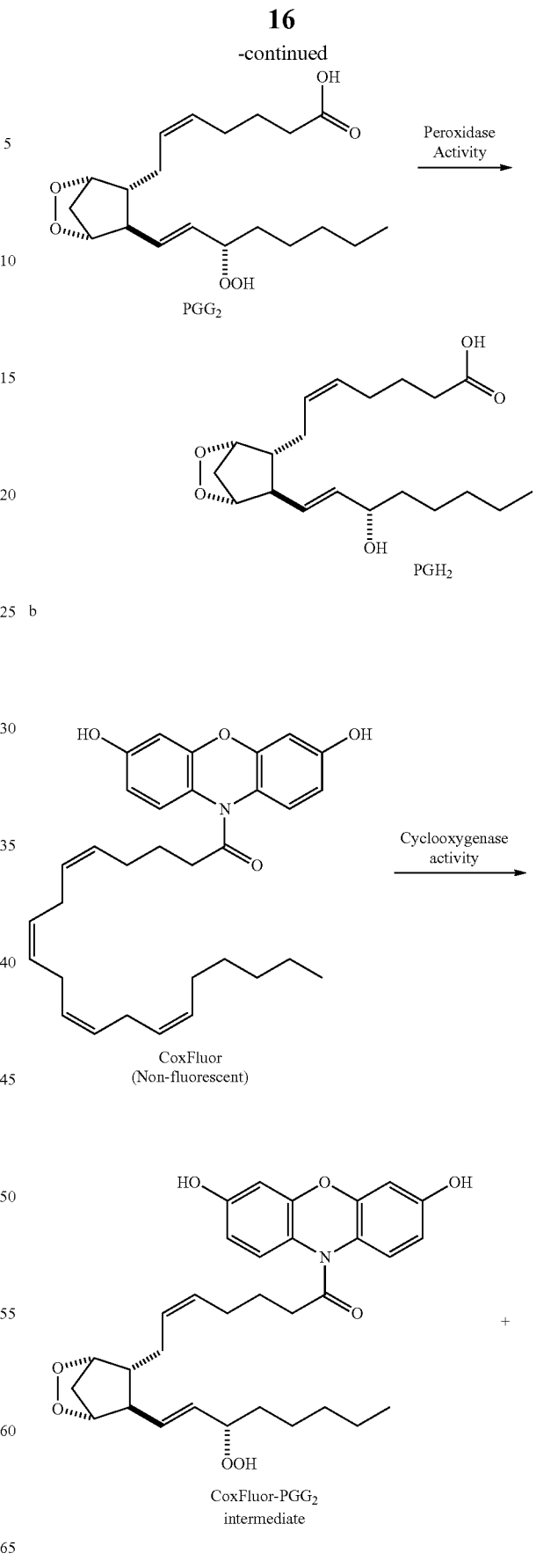

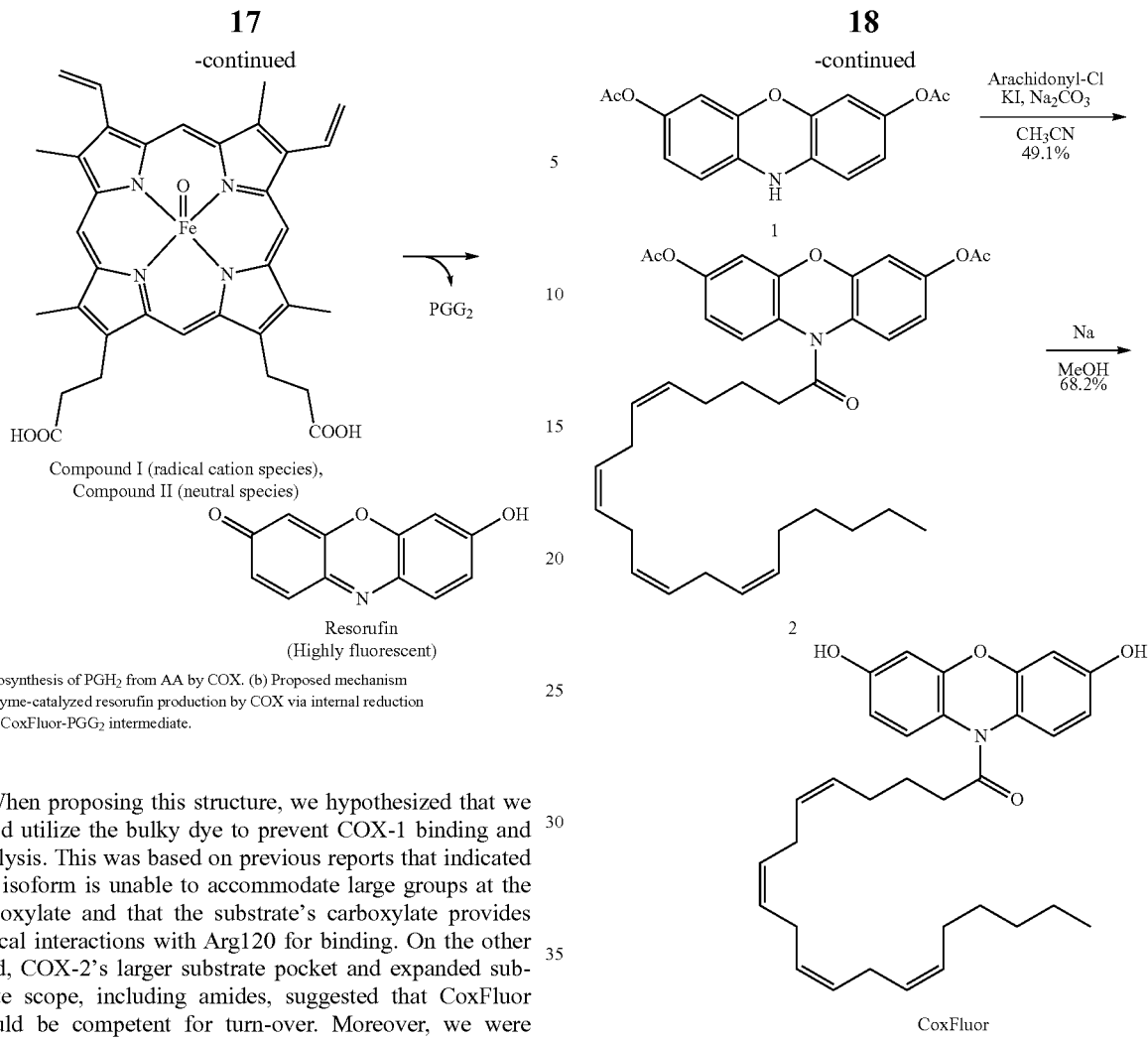

Compound I (radical cation species),
Compound II (neutral species)

Resorufin
(Highly fluorescent)

(a) Biosynthesis of PGH$_2$ from AA by COX. (b) Proposed mechanism of enzyme-catalyzed resorufin production by COX via internal reduction of the CoxFluor-PGG$_2$ intermediate.

When proposing this structure, we hypothesized that we could utilize the bulky dye to prevent COX-1 binding and catalysis. This was based on previous reports that indicated this isoform is unable to accommodate large groups at the carboxylate and that the substrate's carboxylate provides critical interactions with Arg120 for binding. On the other hand, COX-2's larger substrate pocket and expanded substrate scope, including amides, suggested that CoxFluor should be competent for turn-over. Moreover, we were intrigued replacing the carboxylate of a COX-1 selective ligand with an amide successfully converted COX-1 inhibitors into selective COX-2 inhibitors.

The synthesis of CoxFluor began with the Zn-mediated reduction of resazurin, followed by acetylation using acetic anhydride to afford compound 1 in 63% yield over two steps. This intermediate was then coupled to arachidonyl chloride in the presence of sodium iodide to afford compound 2 in 49% yield. Finally, treatment of compound 2 with sodium methoxide (generated in situ) facilitated acetyl deprotection and provided CoxFluor in 68% yield (overall 21% over 4 steps, Scheme 2).

Scheme 2: Synthesis of CoxFluor from resazurin.

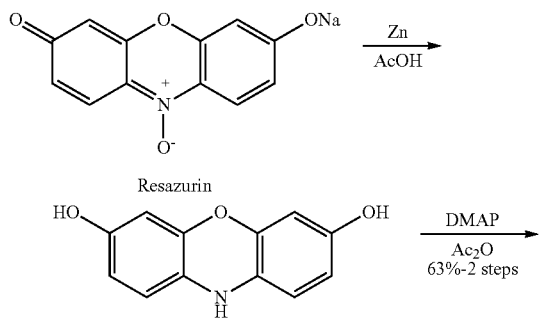

CoxFluor

In Vitro Characterization. With CoxFluor in hand, we first evaluated its response to recombinant human COX-2 (expression and purification details provided in the Examples). Treatment of CoxFluor ($\Phi_F$=0.29, $\varepsilon$=820 M$^{-1}$cm$^{-1}$ at 572 nm) with COX-2 resulted in the production of resorufin ($\Phi_F$=0.55, $\varepsilon$=73,000 M$^{-1}$cm$^{-1}$ at 573 nm, confirmed by LC-MS) and a 41-fold fluorescent turn-on response (FIG. 1a). To confirm that activation was a consequence of enzyme-catalyzed oxidation, rather than unbiased peroxidase activity, we prepared a control compound, Ctrl-CoxFluor, where the AA lipid was replaced with the saturated lipid tail (arachidic acid, synthetic details can be found in the Examples). Ctrl-CoxFluor proved to be unreactive under the same reaction conditions, strongly suggesting that the signal enhancement observed for CoxFluor was due to enzymatic activity. This result also argues against the other possible mechanism where the phenol is directly oxidized by the Tyr385 radical, although a lack of cyclooxygenase binding would yield the same result (Scheme 1).

Under steady state conditions, CoxFluor underwent oxidation to resorufin by COX-2 with a k$_{cat}$ of 19 min$^{-1}$ and K$_m$ of 22 µM (FIG. 1c). The Km values are similar to those obtained for arachidonyl ethanolamide (K$_m$=24 µM) and were within an order of magnitude for AA (Km=6 µM). Direct comparisons for k$_{cat}$ are difficult because COX-2 activity is typically reported for only the cyclooxygenase activity while CoxFluor requires both cyclooxygenase and peroxidase activity for resorufin release. Even so, the measured rate for turnover is within 100-fold of the natural substrate cyclooxygenase activity. Moreover, both indomethacin and celecoxib inhibited COX-2 activity, confirming that CoxFluor can identify and/or evaluate COX-2 inhibitors (FIG. 1d). This overcomes key drawbacks in existing methodology that require radiolabeled compounds (substrate or selective inhibitors), purification of intermediates or products, or coupled-enzyme systems. This also provides further support for the formation of a CoxFluor-PGG$_2$ intermediate because both inhibitors bind within the cyclooxygenase active site of the protein.

Figure 2:
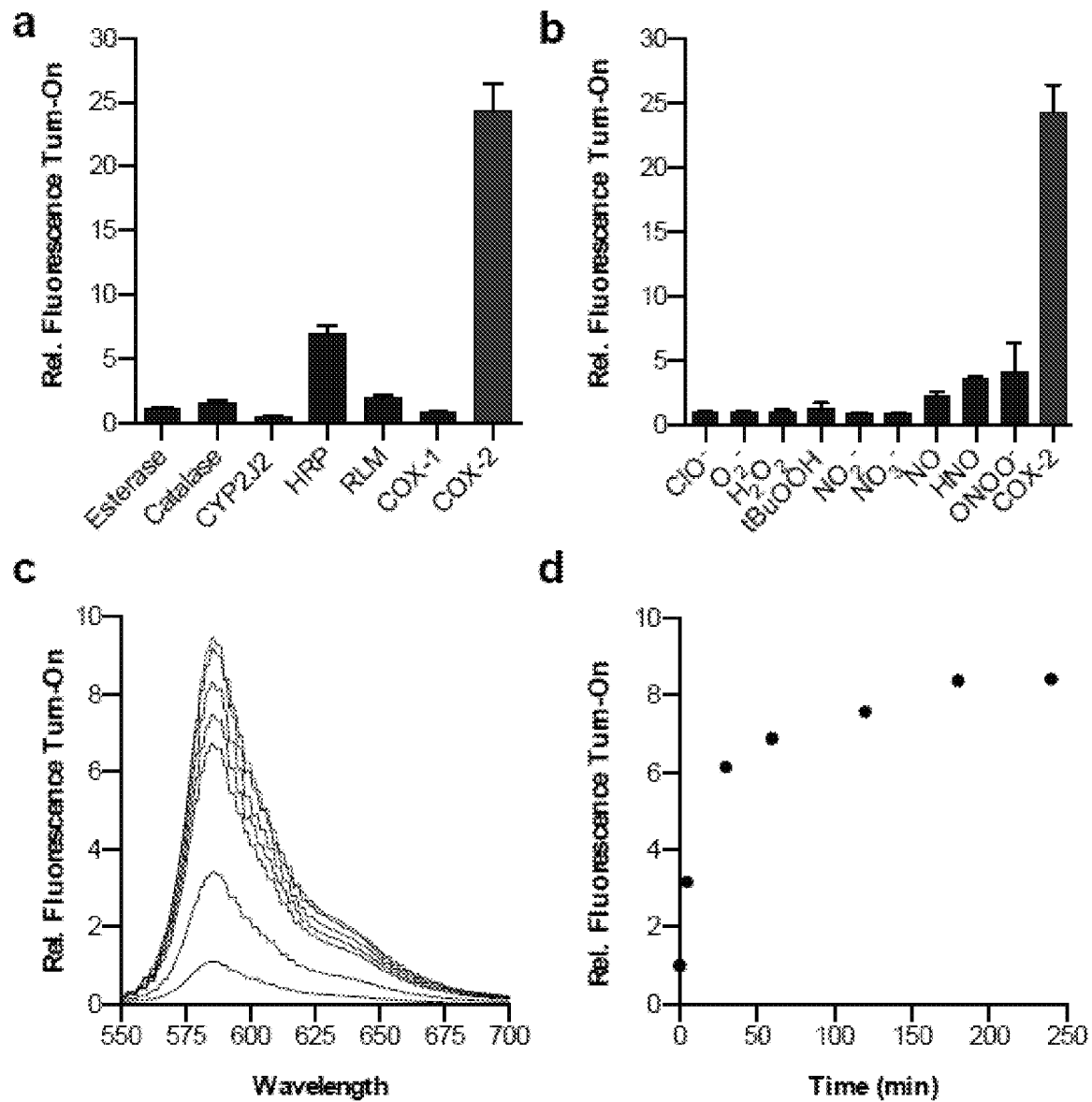
FIG. 2. Relative fluorescence for CoxFluor incubated (a) COX-2 (0.101 U), a panel of enzymes (1.01 U, 10-fold excess) or (b) panel of reactive oxygen/nitrogen species (500 μM, 50 equiv). (c) Relative fluorescence emission spectra and (d) emission at 590 nm for CoxFluor in the presence of glutathione (1 mM) and COX-2 (250 nM). All experiments were conducted at room temperature in 100 mM Tris HCl buffer (pH 8.0) with 10 μM CoxFluor and 1 μM hemin. Values are reported as the mean±standard deviation (n=3) for parts a and b. Parts a-b and c-d were performed according to the plate reader assays and fluorimeter, respectively.
Figure 4:
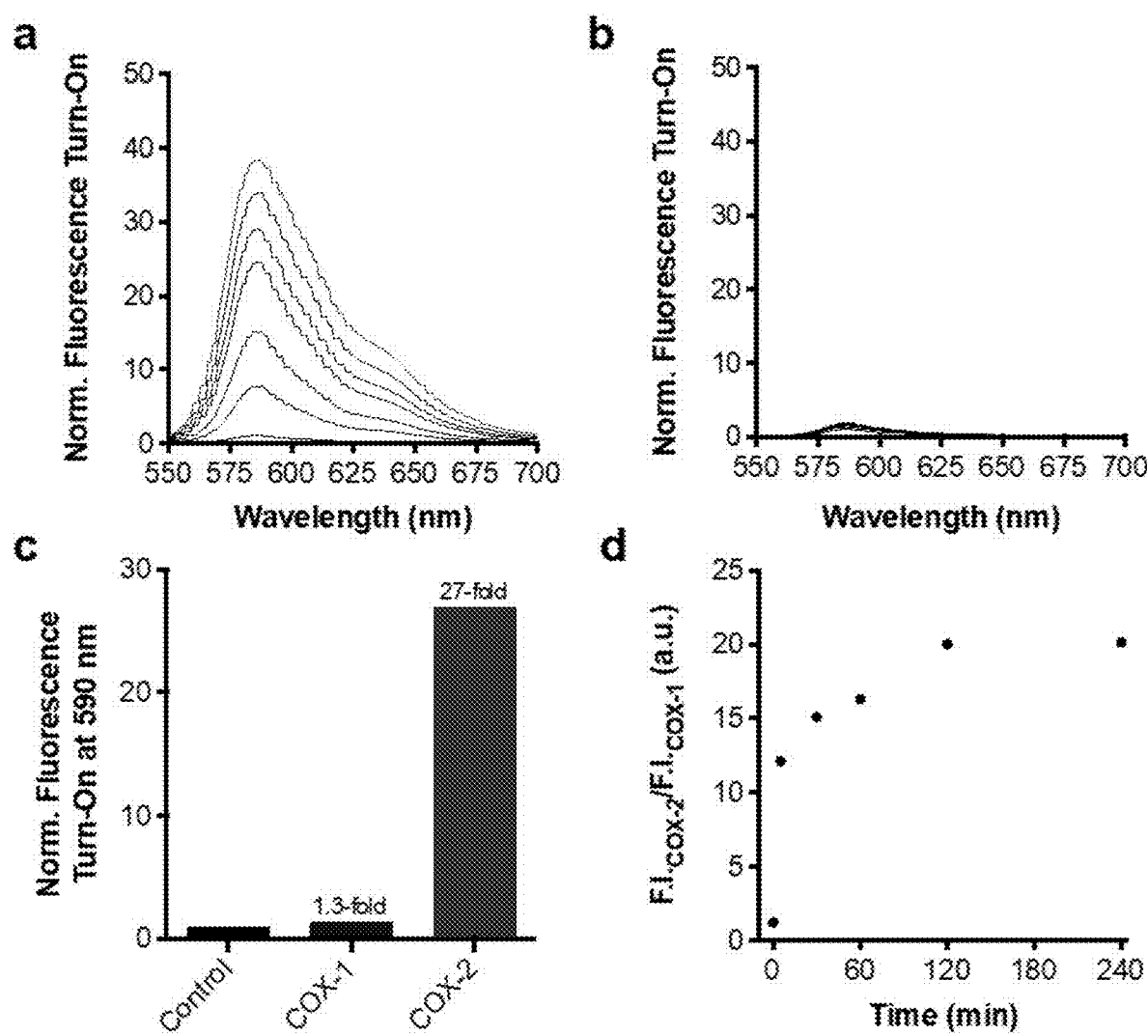
FIG. 4. Representative time-course of CoxFluor fluorescence spectra after treatment with (a) COX-2 or (b) COX-1 over 4 h (uppermost line indicates final time point, normalized to initial timepoint). (c) Comparison of final fluorescence intensity at 590 nm for CoxFluor treated with COX-2 or COX-1 relative to a buffer control. (d) Relative selectivity for COX-2 over COX-1 as a function of time. Reactions were performed at room temperature using the fluorimeter assay protocol (submicroquartz cuvettes) with 10 mM CoxFluor and 250 nM enzyme (COX-1 specific activity is 1.3-fold greater than COX-2 at this concentration) in 100 mM Tris-HCl (pH 8.0).
Figure 5:
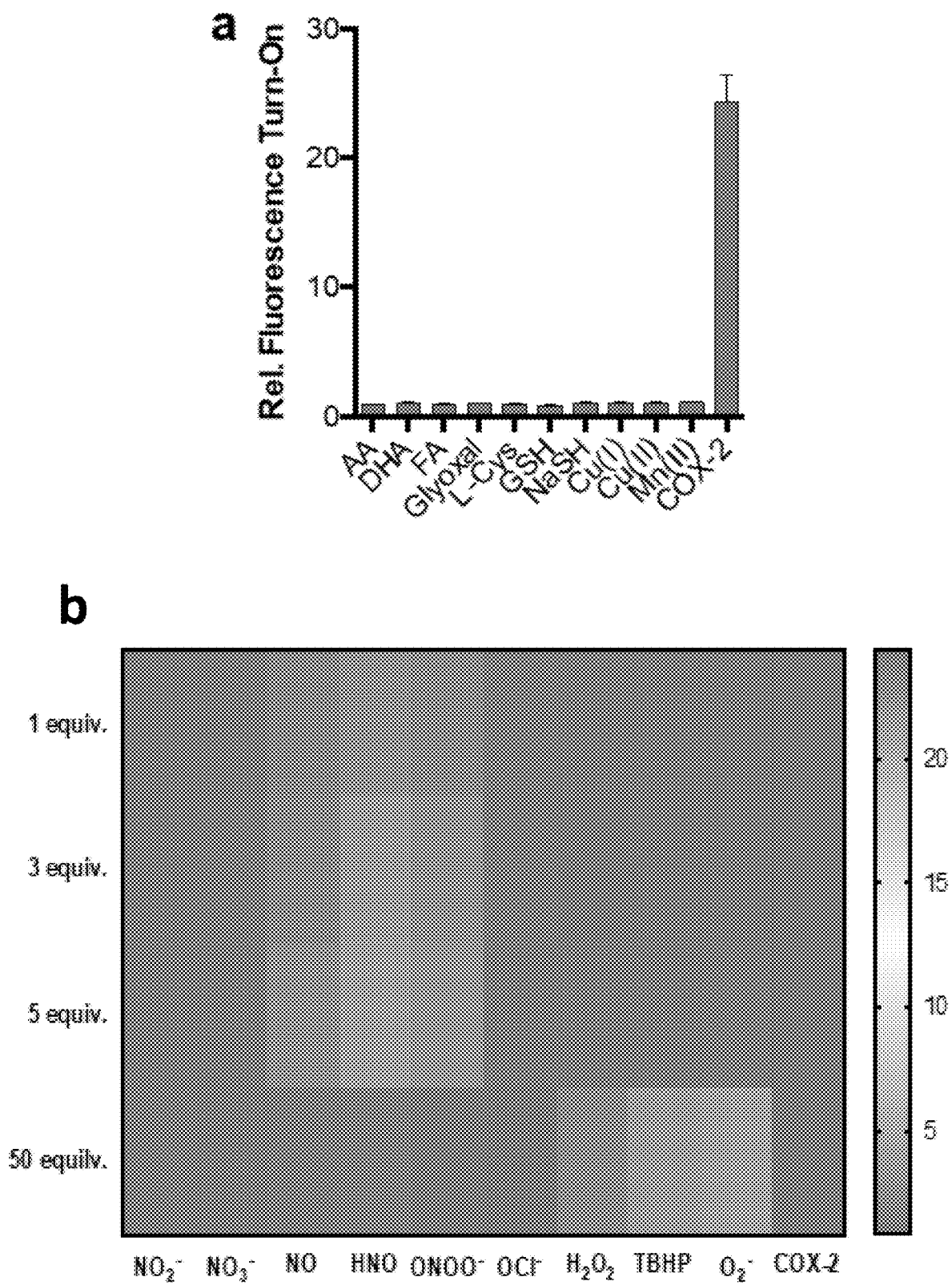
FIG. 5. (a) CoxFluor response to reactive carbonyl (AA: ascorbic acid; DHA: dehydroascorbic acid; FA: formaldehyde; glyoxal), reactive thiols (L-cysteine; GSH: reduced glutathione; NaSH), and metal species (500 μM, 50 equiv). (b) Heat map of the mean fluorescence enhancement of CoxFluor following treatment with 1, 3, 5, or 50 equivalents of RNS or ROS. (c) Representative time course of the relative turn on for COX-2 (250 nM, steepest line) compared to a range of ROS and RNS (5 equivalents). The same results were observed for all other analyte concentrations. (d) Stability of resorufin in the presence of 1, 3, 5, and 50 equivalents of ROS and RNS. Fluorescence enhancements were measured for CoxFluor or resorufin (10 μM) using the plate reader assay. Endpoint assays were performed at 4 h and the fluorescence enhancement was calculated relative to a buffer control (100 mM Tris-HCl, pH 8.0) at the corresponding time point. Values are reported as the mean±standard deviation (n=3).
Figure 5:
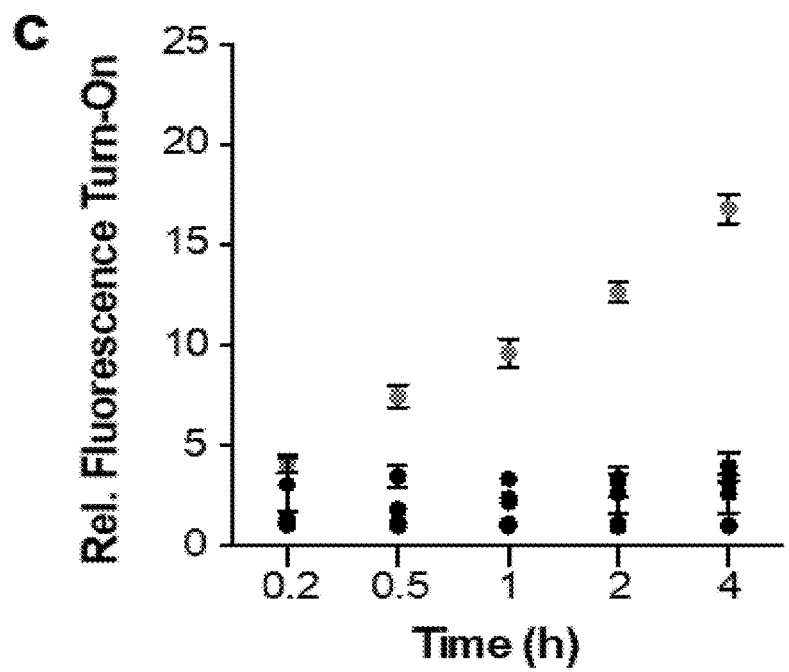
Figure 5:
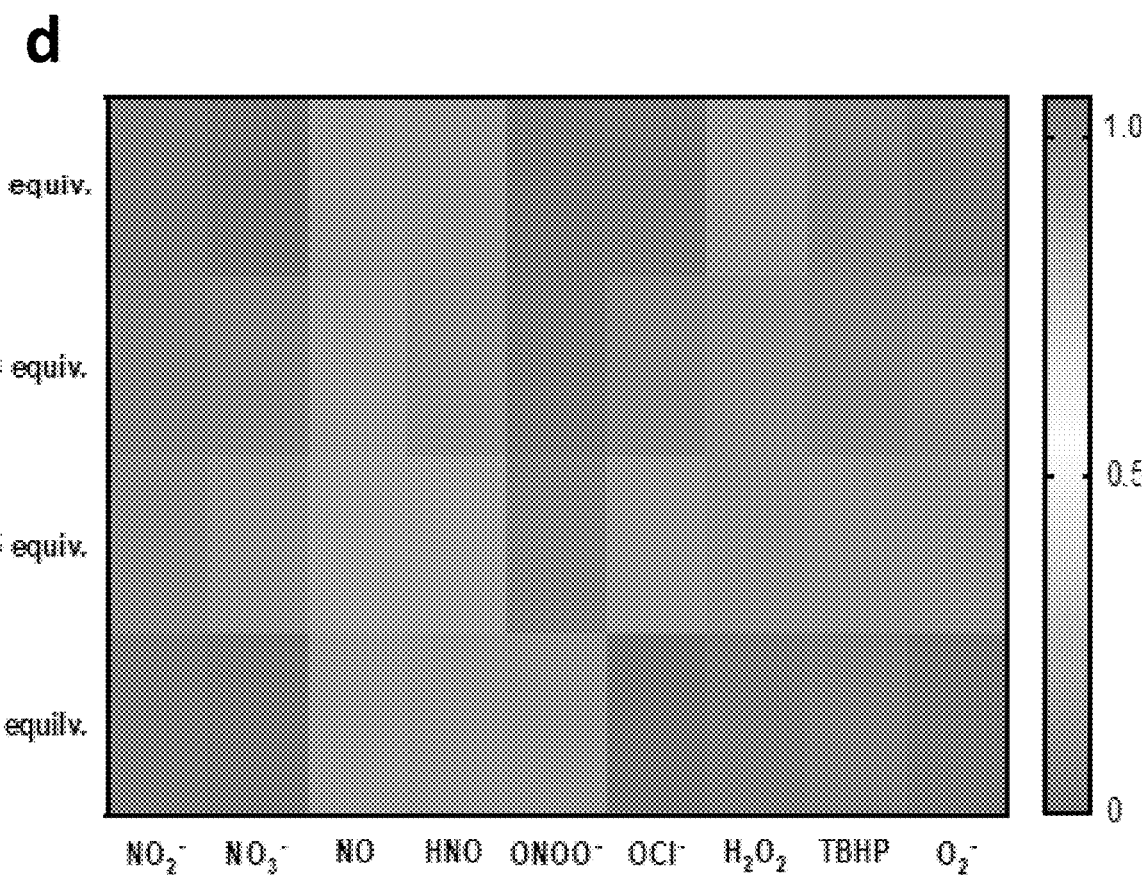

Isoform selectivity was evaluated by incubating CoxFluor with COX-1 isolated from bovine vesicles. No fluorescent enhancement was observed, even in the presence of 10-fold excess enzyme activity (FIG. 2a and FIG. 4). This result confirmed that the steric bulk associated with the 3,7-dihydroxyphenoxazine and lack of carboxylate were sufficient to prevent binding and catalysis by COX-1. Off-target activation was also assessed against a panel of enzymes including horseradish peroxidase, bovine catalase, porcine esterase, human CYP2J2 (with cytochrome reductase), as well as other cytochrome P450 enzymes found in rat liver microsomes. These enzymes were specifically selected because they possess closely related activities (peroxidase, catalase), could potentially cleave the amide (esterase), or are capable of metabolizing AA analogs (cytochrome P450s). Even in the presence of 10-fold excess protein, CoxFluor displayed good selectivity against all of the tested enzymes (FIG. 2a). Likewise, no undesirable activation was observed when CoxFluor was incubated with various biologically relevant reactive oxygen species (e.g., hydrogen peroxide, superoxide), reactive nitrogen species (e.g., peroxynitrite, nitric oxide), and other reactive oxidants and reductants (FIG. 2b and FIG. 5). Importantly, incubation of CoxFluor with COX-2 in the presence of glutathione (1 mM) maintained significant COX-2-specific fluorescence enhancements indicating the potential for use for live-cell imaging (FIG. 2c). This is in contrast to Amplex® Red-based assays, which displays cross-reactivity with glutathione in the presence of peroxidase activity or direct quenching of the radical intermediate.

Figure 6:
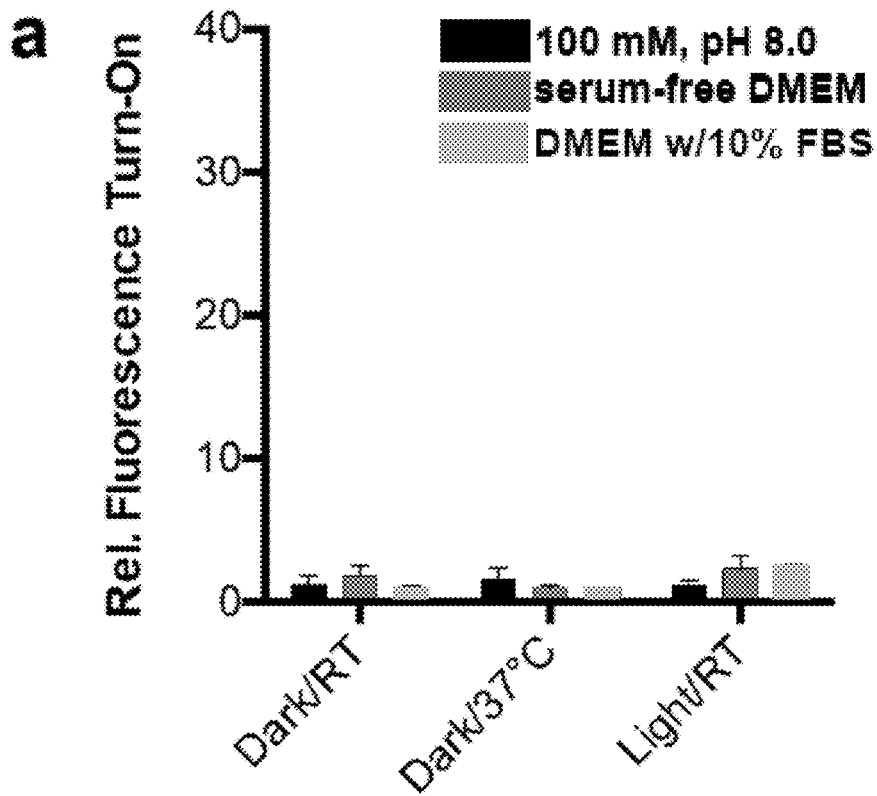
FIG. 6. Stability of (a) CoxFluor and (b) resorufin in Tris-HCl (100 mM, pH 8.0, (left bar) and serum-free DMEM (middle bar), DMEM with 10% FBS (right bar) after 8 h at room temperature with or without exposure to ambient light. Values are reported as the mean±standard deviation (n=3).
Figure 6:
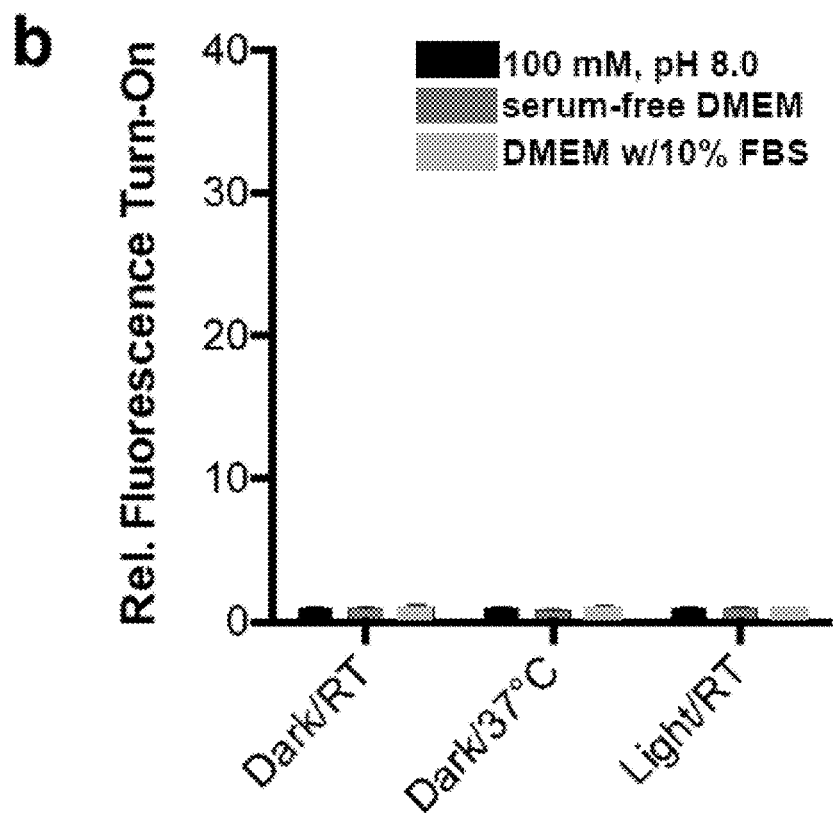
Figure 7:
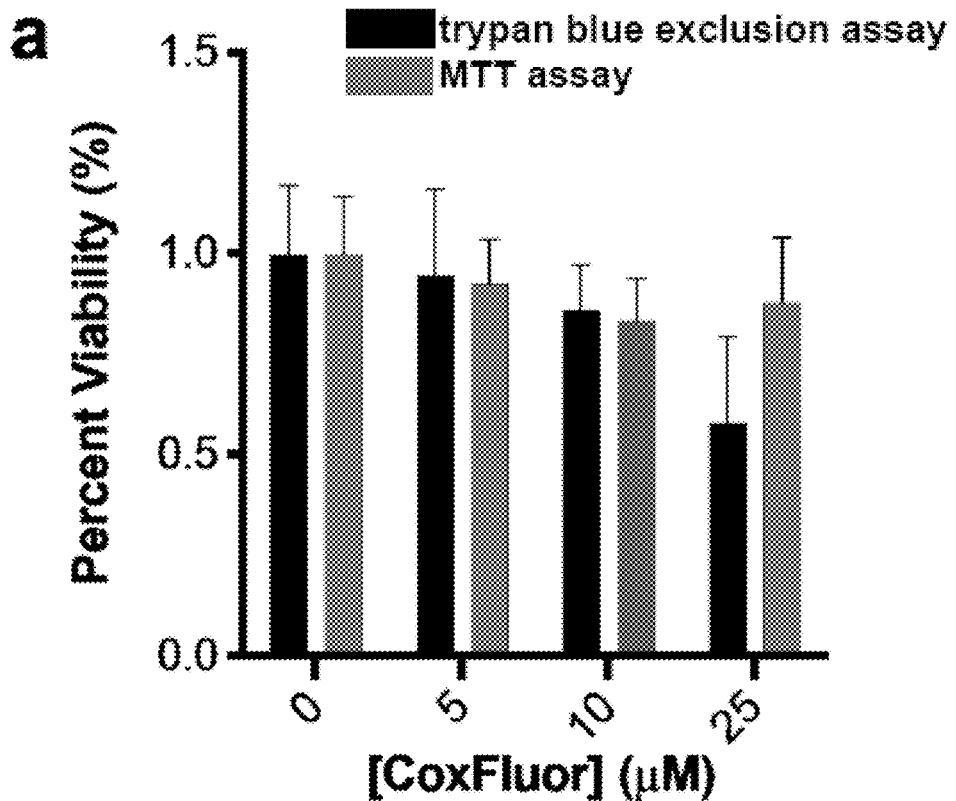
FIG. 7. Cell viability for CoxFluor in (a) HEK 293T cells and (b) RAW 264.7 macrophage cells after 6 h incubation as measured by the trypan blue exclusion assay (black) and MTT assay (grey). Values are reported as the mean±standard deviation (n=3).
Figure 7:
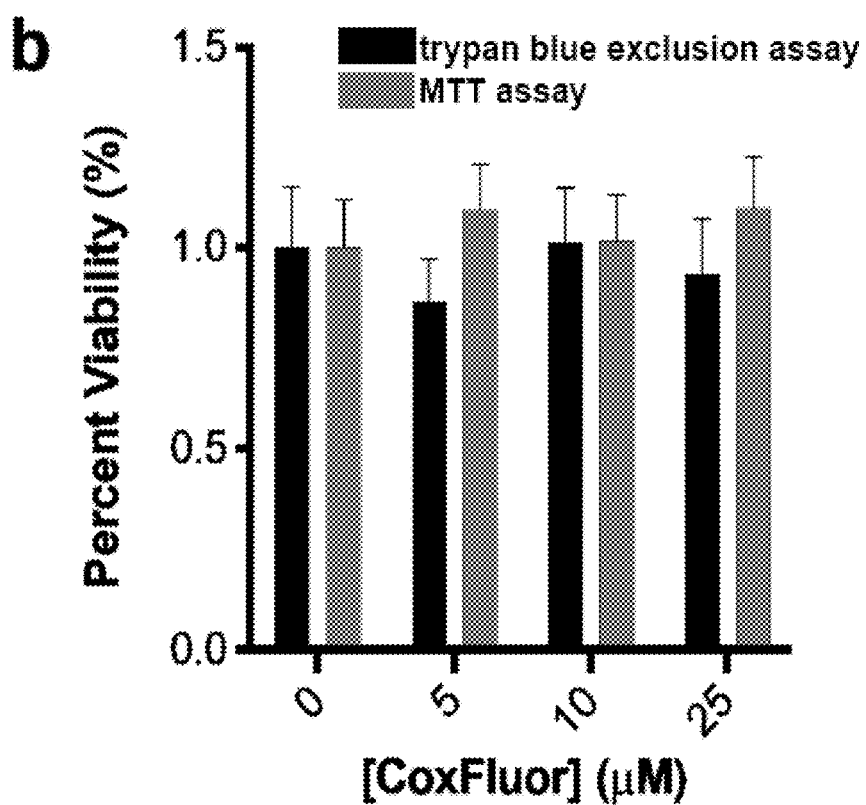

Live-Cell Imaging of COX-2 Activity. Due to the promising results, we were interested in applying CoxFluor for the detection of COX-2 activity in live cells. Before performing imaging experiments, stability and biocompatibility were evaluated. CoxFluor and resorufin were both stable in Tris-HCl and DMEM buffer systems with negligible increases after 8 hours incubation at room temperature or 37° C. (with or without ambient light, FIG. 6). Additionally, we found that the probe showed suitable viability in HEK 293T cells and RAW macrophage cells (FIG. 7).

Figure 3:
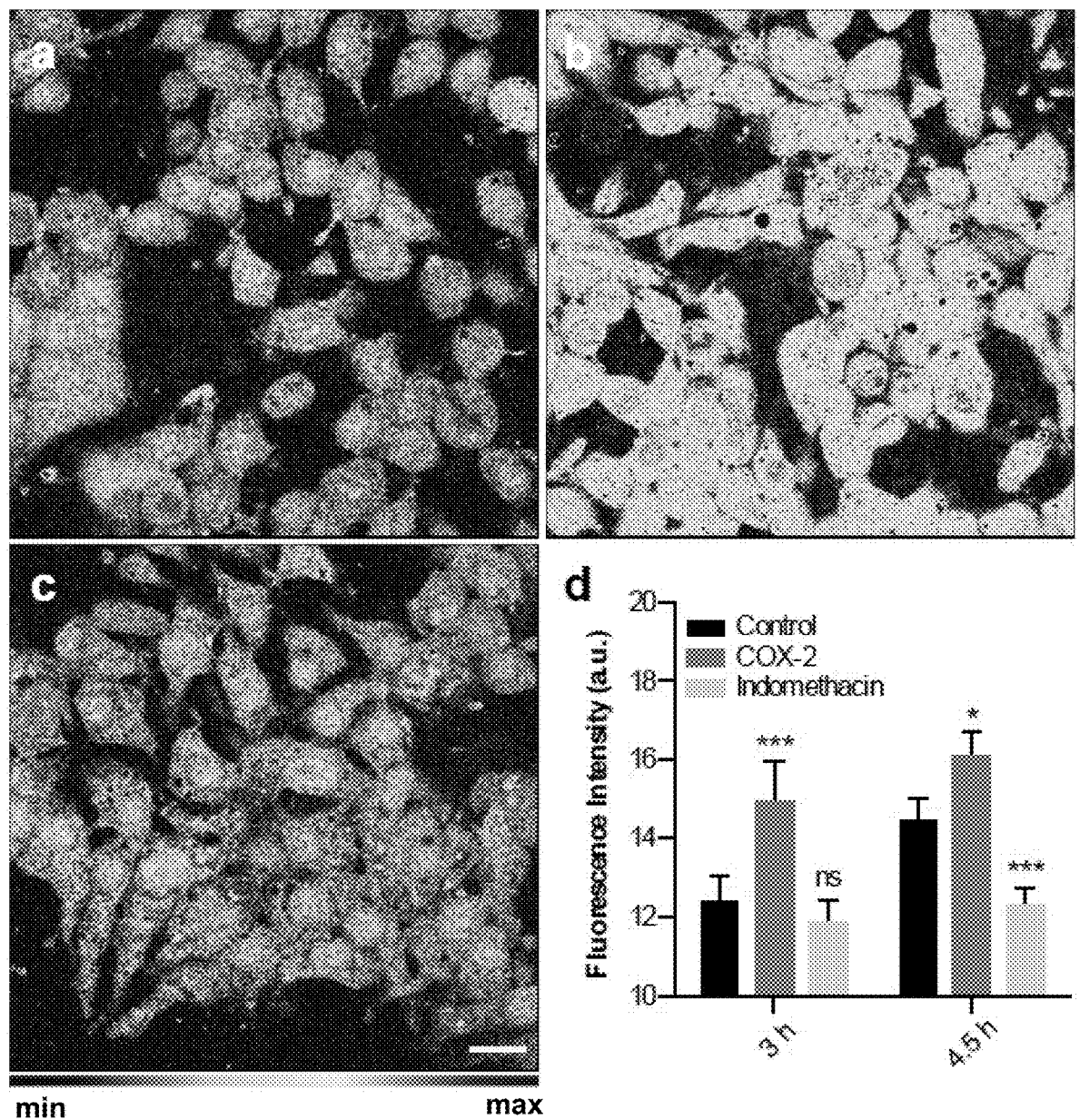
FIG. 3. Confocal imaging of COX-2 activity in (a) control, (b) transfected, and (c) indomethacin-treated transfected HEK 293T cells after 3 h incubation with CoxFluor (10 μM) at 37° C. Scale bar represents 10 μm. (d) Quantification of images at 3 and 4.5 timepoints. Statistical analysis was performed using 2-way ANOVA (α=0.05). Fluorescence intensities were compared to the control at each time point using Sidak's multiple comparison test (α=0.05). *, p<0.05; ***, p<0.001.
Figure 8:
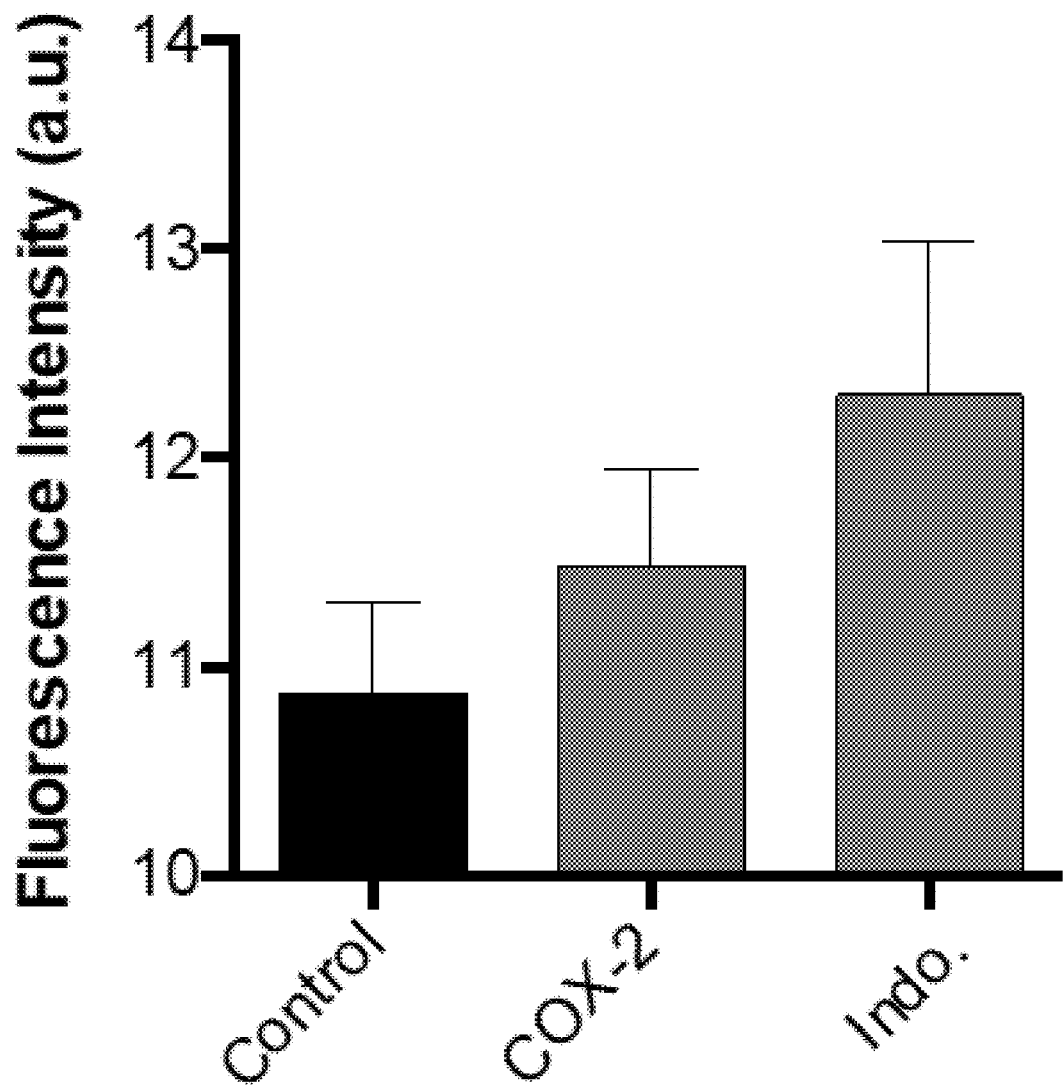
FIG. 8. Quantified confocal imaging of COX-2 activity after 3 h incubation in either non-transfected (control) or transfected HEK 293T cells. Indomethacin inhibition (Indo., 10 µM) was performed in transfected cells. Values are reported as the mean±standard deviation (n=3).

Having demonstrated the requisite stability, biocompatibility, selectivity, and sensitivity we turned our attention to applying CoxFluor to image COX-2 activity within live cells. Specifically, we generated a transiently transfected HEK 293T cell line over-expressing human COX-2. We performed a glutathione depletion with N-ethylmaleimide prior to staining to limit glutathione effects because glutathione can generate or quench radical intermediates of other peroxidase-based probes complicating the interpretation of the results. Moreover, past work has demonstrated that COX-2 inhibitors (e.g., celecoxib analogs and indomethacin) can decrease glutathione levels within B cells and in indomethacin-induced gastric mucosa lesion rat models, which we have experimentally confirmed (FIG. 8). After incubation with CoxFluor for 3 h we observed a 1.2-fold increase for transfected cells, as compared to the control, and no fluorescence enhancement was observed upon treatment with indomethacin (FIG. 3a-d). It is important to note that extending the incubation time to 4.5 h resulted in a 1.2-fold fluorescence enhancement for the control, relative to indomethacin-treated transfected cells, demonstrating that CoxFluor can detect endogenous COX-2 (FIG. 3d).

Figure 9:
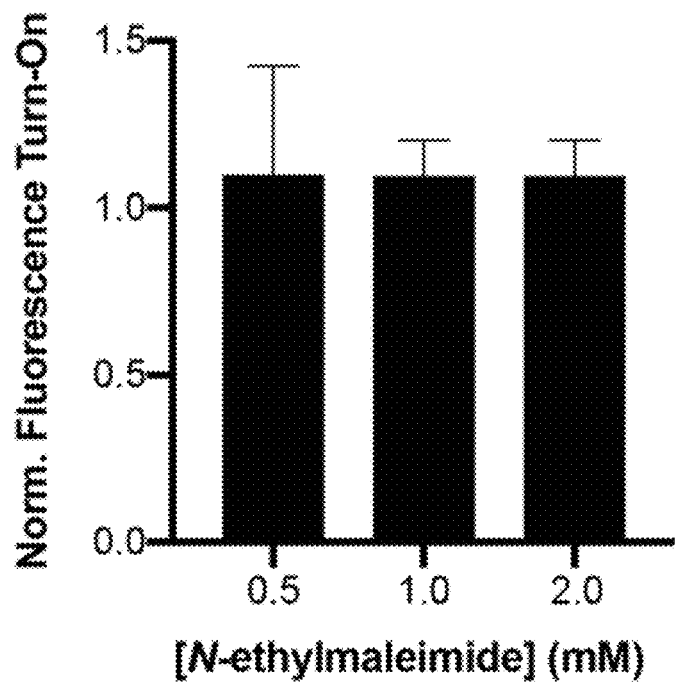
FIG. 9. Normalized fluorescence response for CoxFluor (10 µM) after incubation with COX-2 (250 nM) at varying concentrations of N-ethylmaleimide. Samples were incubated at room temperature for 4 h and normalized to the fluorescence with 0 mM N-ethylmaleimide. Assay was performed according to the plate reader assay. Values are reported as the mean±standard deviation (n=3).
Figure 10:
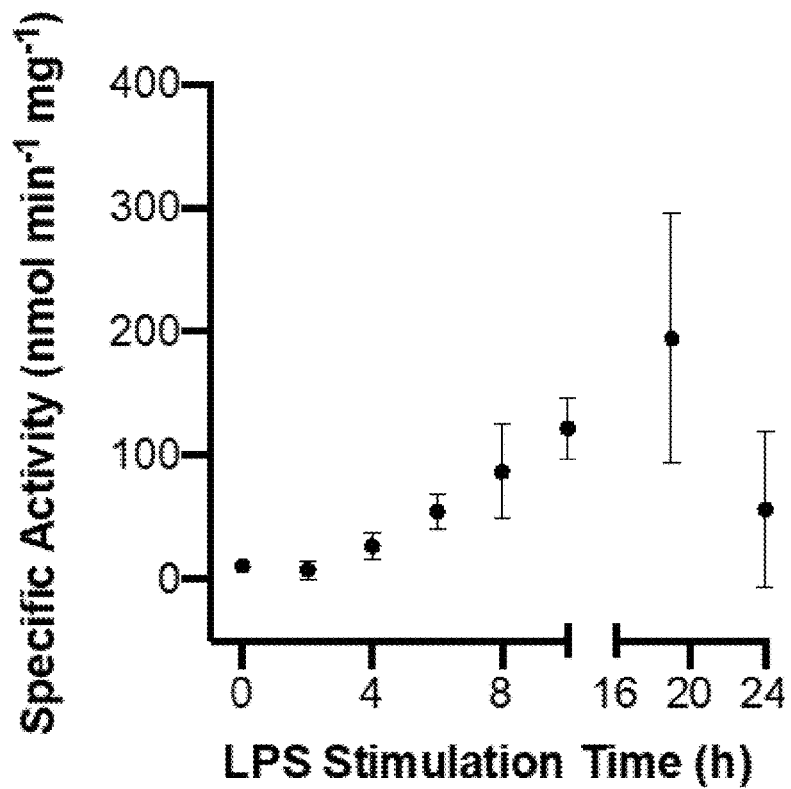
FIG. 10. RAW 264.7 macrophage cell lysate COX-2 activity as a function of LPS stimulation time. Enzymatic activity was measured at room temperature with CoxFluor (10 µM) in 89 mM Tris-HCl buffer (pH 8.0) containing 10% CelLytic M and 1 mM N-ethylmaleimide. Initial rates were measured within the linear region (typically the first 30 seconds) and protein concentration was measured using the BCA assay. Values are reported as the mean±standard deviation (n=3).
Figure 13:
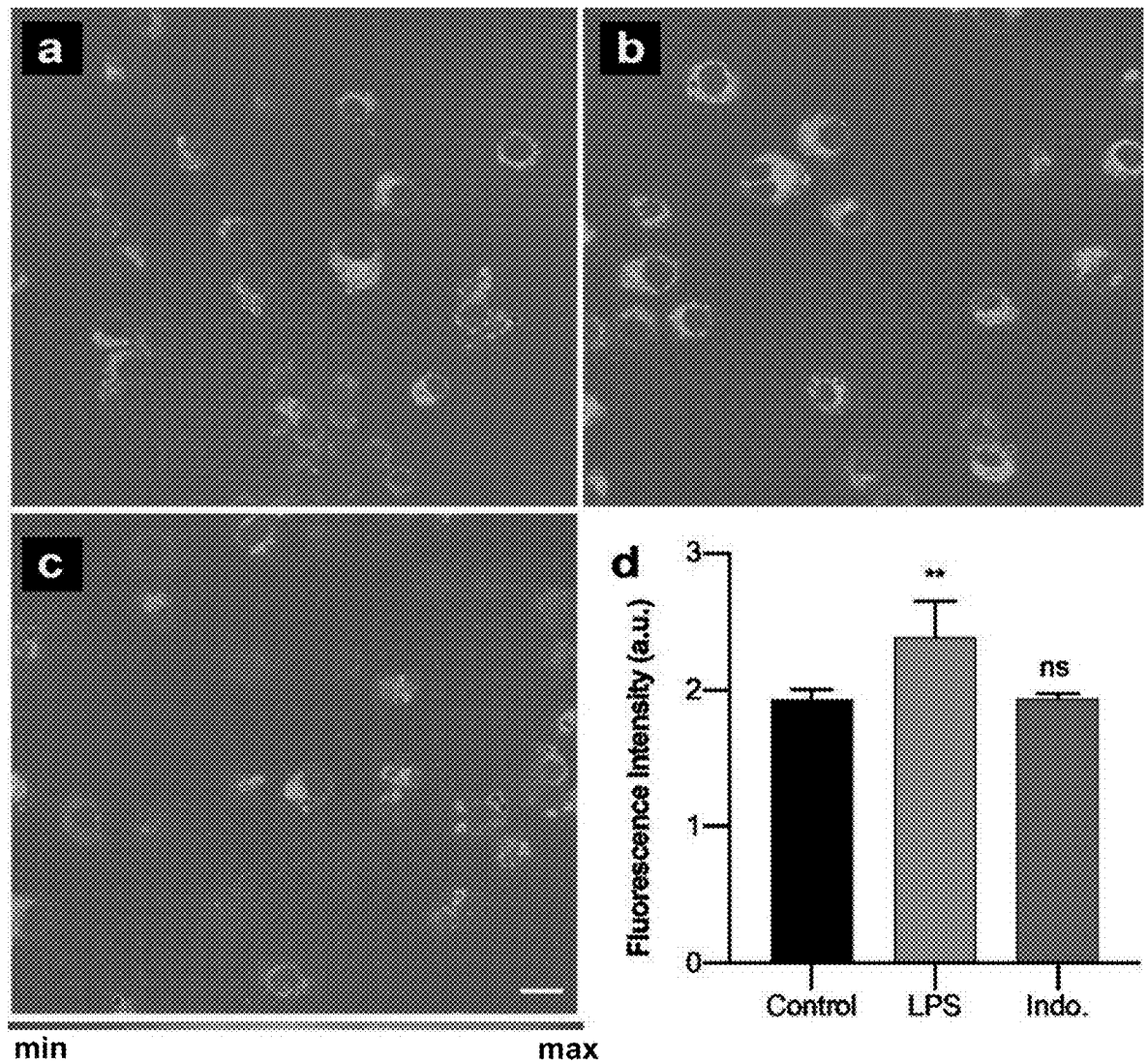
FIG. 13. Confocal imaging of COX-2 activity in a) control, b) LPS-stimulated (1 µg mL$^{-1}$), and c) indomethacin-treated (10 µm), LPS stimulated RAW 264.7 cells after 4 h incubation with CoxFluor (10 µm) at 37° C. following treatment with BSO (began 2 h prior to staining, 200 µm). Scale bar=10 µm (white bar). d) Quantified data. Values are reported as the mean±standard deviation (n=3). Statistical analysis was performed using one-way ANOVA ($\alpha=0.05$). **, $p<0.01$.

Next, we applied CoxFluor for the detection and imaging of endogenous COX-2 activity within RAW 264.7 macrophage cells. To date, these studies typically rely on mRNA quantification, western blot analysis, or downstream product quantification (e.g., ELISA assays) rather than direct quantification of COX-2 activity. This is due to the lack of isoform selectivity in current cyclooxygenase assays. First, we measured the effect of LPS stimulation time on COX-2's specific activity in RAW 264.7 macrophage lysates. Variations due to GSH fluctuations were again minimized using NEM, which we and others have shown does not affect COX activity (FIG. 9). Only a modest 2.4-fold increase in COX-2 activity was observed within the first 4 hr of activation. Over the next several hours, the activity increased in a linear fashion to a maximum of 17.6-fold at 19 hr (FIG. 10). The activity differences were then confirmed within live cells using confocal microscopy where we observed a 1.2-fold fluorescent enhancement for LPS-stimulated cells relative to the control (FIG. 13). Rather than using NEM, we pre-treated with buthionine sulfoximine (BSO), a γ-glutamyl-cysteine synthase inhibitor because it is a less cytotoxic alternative.

Figure 11:
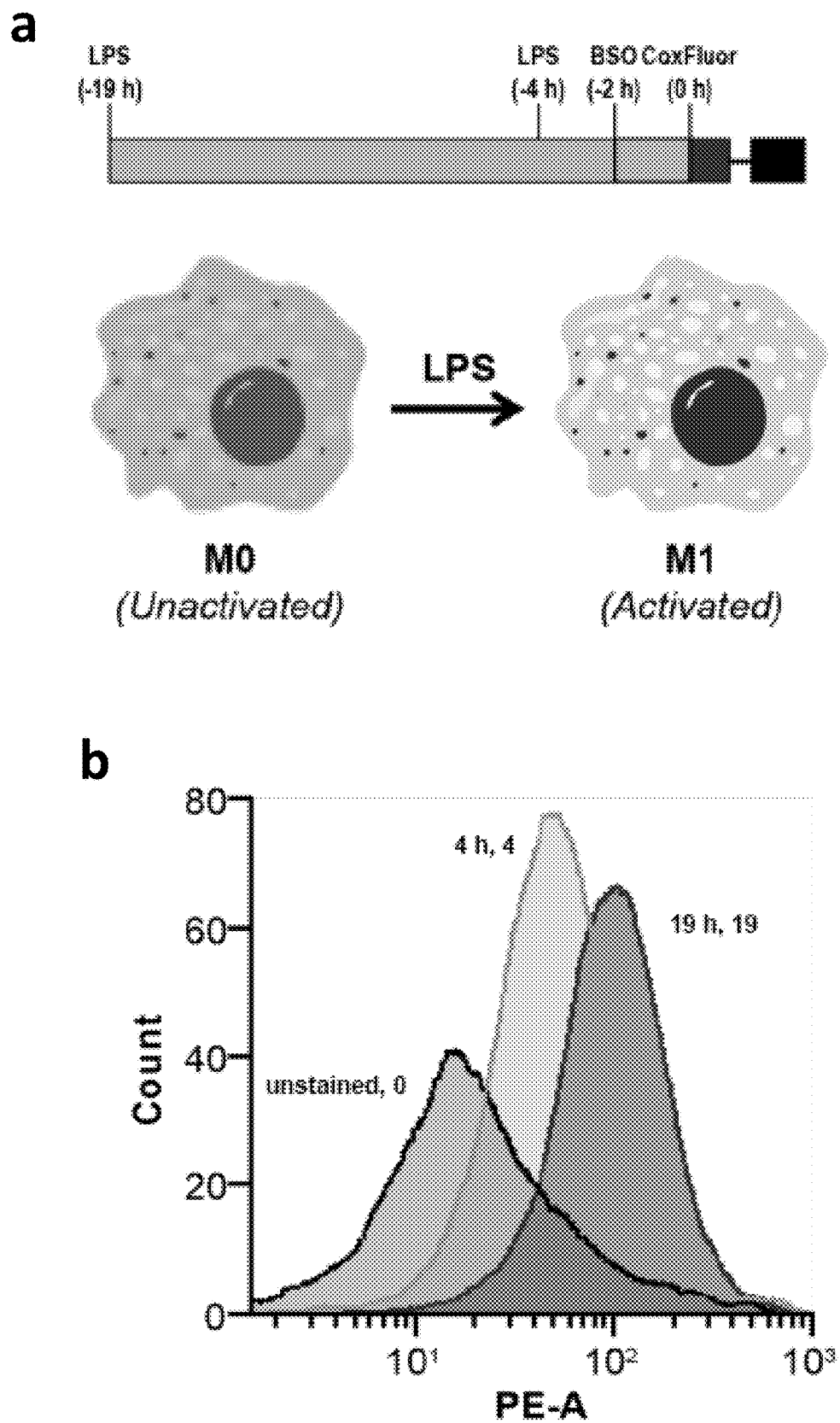
FIG. 11. (a) A schematic representation of the protocol for measuring time-dependent changes in LPS-activated RAW 264.7 macrophage COX-2 activity with flow cytometry. (b) Representative histogram and (c) quantified median fluorescence for unstained (0 hr), and CoxFluor stained cells after 4 h (4 hr) and 19 h (19 hr) LPS activation. (d) Quantified ratio of median fluorescence between cells stained with CoxFluor to cells stained with CoxFluor in the presence of indomethacin (20 µM). All staining was performed with 10 µM CoxFluor, 200 µM BSO was added 2 h prior to staining, and values are reported as the mean±standard deviation (n=3). Statistical analysis was performed using a 2-way ANOVA ($\alpha=0.05$) with Tukey's multiple t test ($\alpha=0.05$) for comparison of 19 h LPS-stimulation to both 0 and 4 h. **, $p<0.01$.
Figure 11:
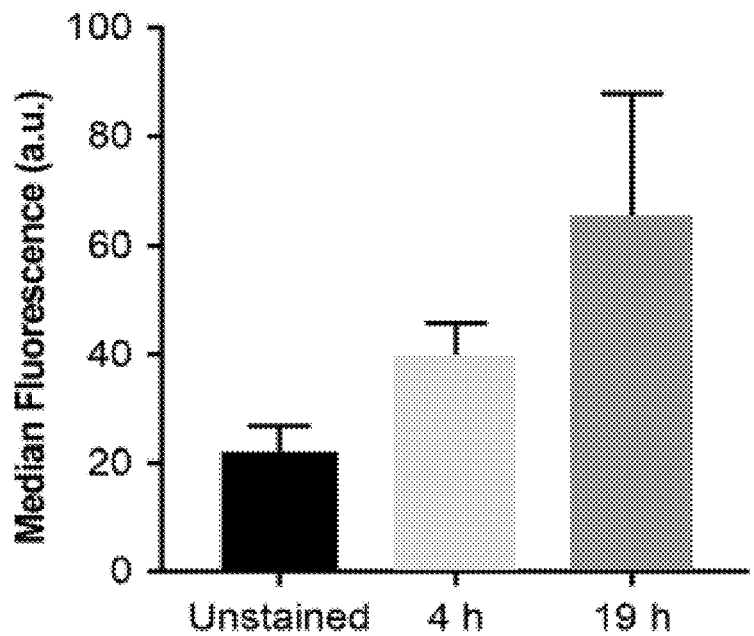
Figure 11:
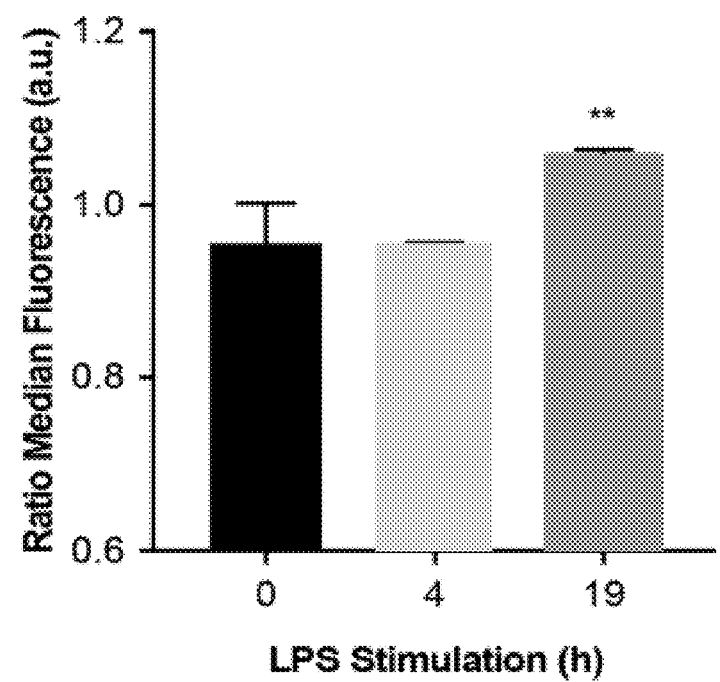
Figure 12:
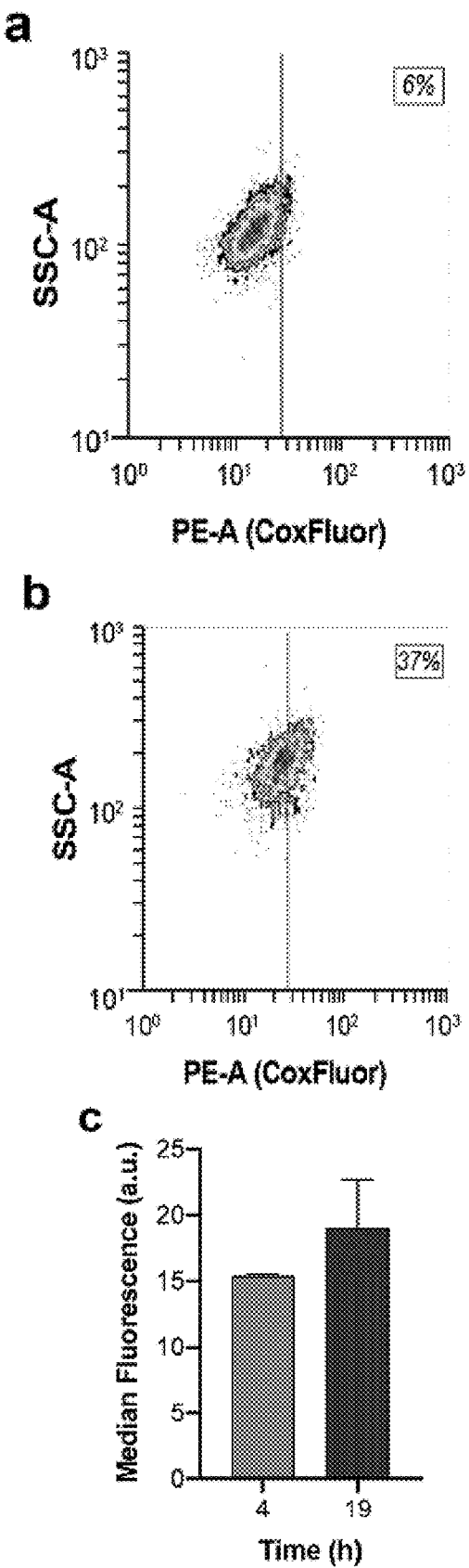
FIG. 12. Representative density plot for LPS-activated RAW 264.7 macrophage cells with flow cytometry without BSO with (a) 4 h or (b) 19 h LPS-stimulation. (c) Quantified median fluorescence for CoxFluor (10 µM) stained cells after 4 (grey) and 19 h (black) LPS activation. Percentages indicate the percent COX-2 positive cells, as defined by the vertical line. Values are reported as the mean±standard deviation (n=3).
Figure 14:
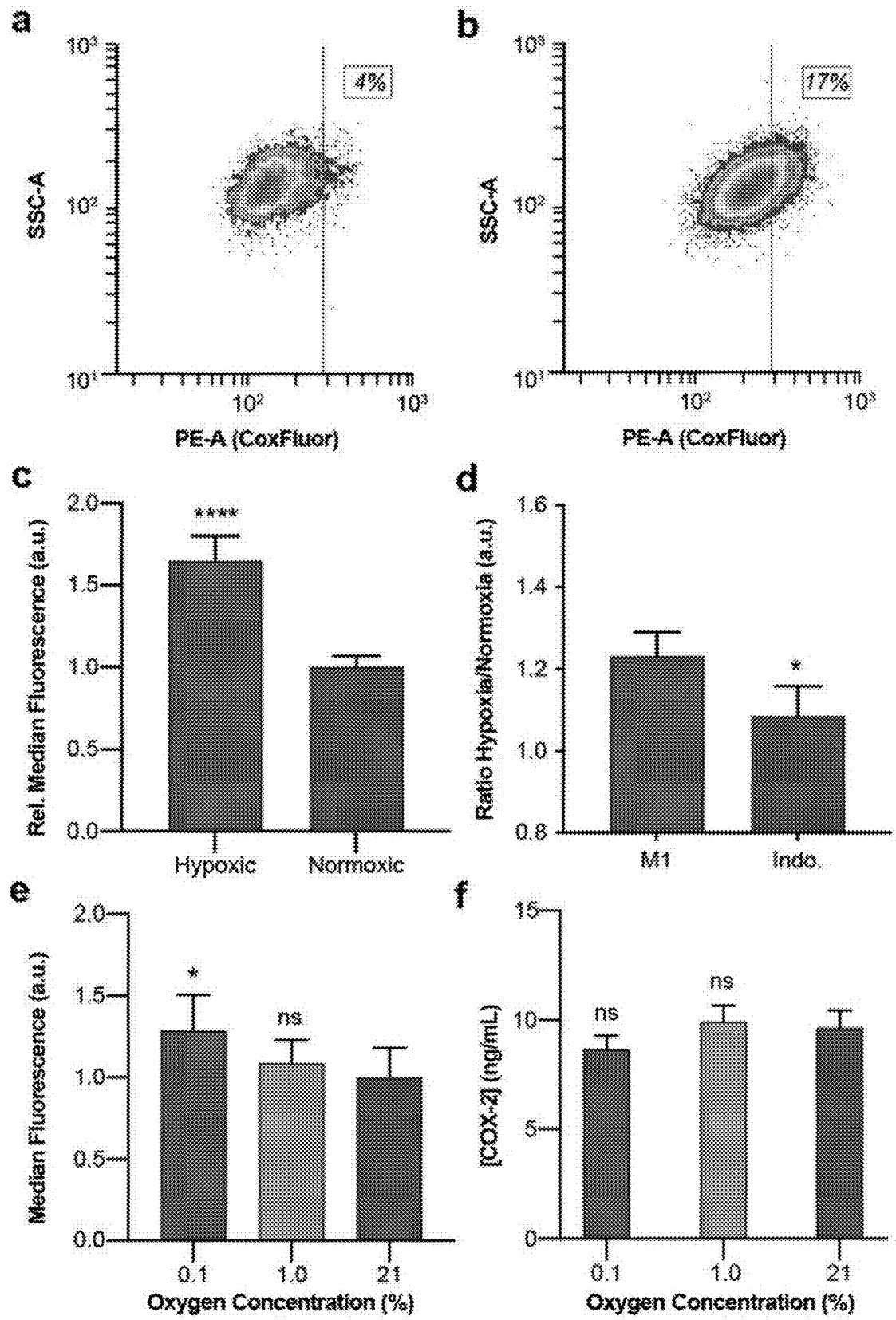
FIG. 14. Contour plots of flow cytometry data from live LPS-activated RAW 264.7 macrophage cells stained with CoxFluor (10 µm) under a) normoxic and b) hypoxic conditions. c) Quantified median fluorescence for hypoxic and normoxic cells. d) Effect of indomethacin (20 µm) treatment on the ratio of hypoxic to normoxic median fluorescence. e) Median fluorescence of RAW 264.7 macrophage cells stained under 0.1%, 1.0%, or 21% oxygen concentrations. f) ELISA quantification of COX-2 protein expression levels in 25 µg mL$^{-1}$ protein lysates. Values are reported as the mean±propagated standard deviation (n=6 for flow cytometry data; n=3 indomethacin inhibition and ELISA data). All staining was performed following treatment with BSO (began 2 h prior to staining, 200 µm) and oxygen dependent flow cytometry data was replicated on two separate days. Statistical analysis was performed with two-tail Student's t test for (c), one-tail Student's t test for (d), or one-way ANOVA for (e) ($\alpha=0.05$). *, $p<0.05$, ****, $p<0.0001$.

Flow Cytometric Analysis of COX-2 Activity. Flow cytometric analyses complete ment live-cell imaging by sampling more of the population, but without the spatial resolution from microscopy. After BSO pre-treatment, observed a 1.6-fold increase in median fluorescence for cells activated for 19 hr as compared to 4 hr. By monitoring the ratio of fluorescence from CoxFluor stained cells to CoxFluor stained cells treated with indomethacin clearly identifies COX-2 activity across activation states (M0 versus M1, FIG. 11). We confirmed that CoxFluor could detect activity changes without GSH depletion where a 1.2-fold increase in activity was observed after 19 hr LPS-activation relative to 4 hr LPS-stimulated cells using flow cytometry (FIG. 12). Finally, we were interested in determining whether COX-2 activity can be regulated beyond the protein level within the native cellular environment. The effect of oxygen on COX-2 activity was evaluated in RAW 264.7 macrophage cells after a 19 hr activation with LPS. The cells were then stained under normoxic (ca. 21%) or hypoxic conditions (prepared using AneroPack for <0.1% oxygen in a sealed container) and the fluorescent response was monitored with flow cytometry. Interestingly, higher activity was observed under hypoxic conditions, as indicated by a substantial shift in the population's median fluorescence (FIG. 14a). Importantly, this increase in fluorescence was COX-2-dependent, where treatment with indomethacin resulted in a 12% decrease in the ratio of median fluorescence for hypoxic to normoxic M1 macrophages (FIG. 14b).

To confirm the result and evaluate the dose-dependence of oxygen, we repeated the experiment under a 1 or 0.1% oxygen atmosphere. In this case, we observe an oxygen-dependent decrease in COX-2 activity as a function of oxygen (FIG. 14c) that is independent of protein expression levels (FIG. 14d). This result provides strong evidence that the local cellular environment plays a critical role in regulating the activity of COX-2. Additional information and data supporting the invention can be found in the following publication by the inventors: *Angew. Chem. Int. Ed.* 2020, 59(8), 3307-3314 and its Supporting Information, which is incorporated herein by reference in its entity.

Conclusion. Due to its widespread biological roles, it is clear why COX remains a prominent target for treating pain, fever, and cancer. COX inhibitors have been widely successful in the clinic where non-steroidal anti-inflammatory drugs represent an expansive class of therapeutics with examples ranging from covalent (aspirin) to allosteric (ibuprofen, naproxen) and competitive (indomethacin) modes of action. While no FDA approved COX-2 inhibitors exist for the treatment of cancer, it remains an active area of research. In conclusion, we have developed CoxFluor, the first isoform-selective fluorescent probe for COX-2 by linking the natural substrate to a resorufin precursor through a sessile amide bond. As a competent substrate for both the cyclooxygenase and peroxidase activities of the catalyst, it was possible to undergo both dioxygenation and cyclization, to afford the CoxFluor-PGG$_2$ intermediate, and oxidation by Compound I or Compound II to release resorufin and PGG$_2$. Molecular dynamic studies support the proposed mechanism and provided structural insights regarding the origin of isoform selectivity. The probe was then utilized to detect and image COX-2 activity in live cells. CoxFluor is therefore a powerful tool for monitoring COX-2 activity, rather than transcription or translation, both in vitro and within live-cells.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

General Synthetic Methods and Materials

Materials. Materials were purchased from commercial vendors and used without further purification. All deuterated solvents were purchased from Cambridge Isotope Laboratories. Isoamyl nitrite was purchased from Acros Organic. Disodium ethylenediaminetetraacetate dihydrate (EDTA) was purchased from Alfa Aesar. 13(S)-HpODE, recombinant human 5-lipoxygenase, and methylamine hexamethylene methylamine NONOate (MAHMA-NONOate) was purchased from Cayman Chemicals. Sodium diethyldithiocarbamate trihydrate (DETC) was purchased from Chem-Impex Incorporated. Corning® Supersomes™ Human Monoamine Oxidase A was purchased from Corning Inc. Acetone, ammonium chloride, Mitsubishi™ Anaero-Pack™-Anaero Anaerobic gas generator, bovine serum albumin (lyophilized), dichloromethane, dimethyl sulfoxide, glacial acetic acid, oxalyl chloride (Acros), phosphate saline buffer (Corning), sodium bicarbonate, sodium carbonate, sodium chloride, sodium hydroxide, sodium perchlorate (monohydrate), and Triton X-100 were purchased from Thermo Fisher Scientific. Anhydrous methanol, conc. hydrochloric acid, and hydrogen peroxide (30% v/v) were purchased from Macron Fine Chemicals. Zinc dust was purchased from Mallinckrodt Incorporated. Acetic anhydride, adenosine triphosphate, anhydrous acetonitrile, anhydrous dichloromethane, anhydrous dimethylformamide, arachidic acid, arachidonic acid, β-nicotinamide adenine dinucleotide 2'-phosphate reduced tetrasodium salt hydrate (NADPH), calcium chloride, catalase from bovine liver (lyophilized), celite 545, copper(II) chloride, esterase from porcine liver (lyophilized), formaldehyde (37% w/w in water), glutathione (reduced), glyoxal (40% w/w in water), hemin from bovine, hexanes, horseradish peroxidase (type 1), L-ascorbic acid, L-cysteine, L-dehydroascorbic acid, lipopolysaccharides from *Escherichia coli* O111:B4 (purified by phenol extraction), manganese(II) chloride, myeloperoxidase from human leukocytes, p-nitrophenylacetate, potassium superoxide, propidium iodide, rat liver microsomes (pooled, male), resazurin, sodium acetate, sodium hydrosulfide (hydrate), sodium metal, tris base, and trypan blue powder were purchased from Millipore-Sigma Aldrich. Porcine hematin was purchased from MP Biomedical LLC. 4-dimethylaminopyridine, potassium iodide, and sodium sulfate (anhydrous) were purchased from Oakwood Chemicals. N-ethylmaleimide was purchased from Pierce Chemical Company. Celecoxib, indomethacin, phenol, and resorufin were purchased from Tokyo Chemical Industry. L-buthionine-(S,R)-sulfoximine was purchased from Toronto Research Chemicals.

Instruments and Software. $^1$H and $^{13}$C NMR spectra were acquired on a Varian 500 or Carver B500 spectrometer. The following abbreviations were used to describe coupling constants: singlet (s), doublet (d), triplet (t), or multiplet (m). Spectra were visualized and analyzed using MestReNova (version 10.0) and referenced to trace non-deuterated solvent. High-resolution mass spectra were acquired on a Waters Q-TOF Ultima ESI mass spectrometer or a Waters Synapt G2-Si ESI/LC-MS spectrometer. Ultraviolet-visible spectroscopy was performed on a Cary 60 or NanoDrop 2000 spectrometer. Fluorescence spectra were acquired on a QuantaMaster-400 scanning spectrofluorometer or Spectra-Max M2 plate reader. Ultraviolet-visible spectroscopy and fluorimetry were performed with a micro fluorescence quartz cuvette (Science Outlet), submircroquartz fluorimeter cell (Starna Cells, Inc.), or 96-well plates (clear or black with flat bottom, Corning). Refractive indices were measured using a RHB-32ATC Brix Refractometer. A Strathkelvin oxygen electrode was used for measuring cyclooxygenase activity. Cells were visualized on an EVOS FL epifluorescence microscope and cellular imaging was performed using a Zeiss LSM 700 confocal microscope. A Countess® II FL Automated Cell Counter was used for cell viability assays. Flow cytometry was performed on a BD LSR Fortessa Flow Cytometry Analyzer. Confocal images and flow data were analyzed using ImageJ (NIH) and FCS Express 6.04, respectively. Data were analyzed using Microsoft Excel and GraphPad Prism (version 6.0 or 8.0) and final figures were prepared in Adobe Illustrator (version 22.0.2).

Synthetic Procedures. Thin-layer chromatography (TLC) was performed on glass-backed TLC plates precoated with silica gel containing an UV254 fluorescent indicator (Macherey-Nagel). TLCs were visualized with a 254/365 nm UV hand-held lamp (UVP). Flash silica gel chromatography was performed using 0.04-0.063 mm 60 M silica (Macherey-Nagel). All glassware used under anhydrous reaction conditions were flame-dried under vacuum and cooled immediately before use.

Example 2

Synthesis of Compounds 10H-phenoxazine-3,7-diyl diacetate (1). The compound was prepared according to the previous report by Kodera and coworkers (Anal. Chem. 2011, 83, 9213). Briefly, a mixture of resazurin (200. mg, 0.796 mmol, 1 equiv) and zinc dust (240. mg, 3.67 mmol, 4.6 equiv) in glacial acetic acid (6 mL) was stirred at room temperature for 2 h under $N_2$ atmosphere in the dark. The reaction was concentrated under inert atmosphere, dissolved in acetone (4 mL) and treated with DMAP (68.4 mg, 0.560 mmol, 0.7 equiv) and then acetic anhydride (0.16 mL, 1.69 mmol, 2.1 equiv) was added dropwise and stirred under $N_2$ atmosphere in the dark for 3 h. After completion, the reaction was concentrated and then purified via silica gel chromatography (eluent: 20% EtOAc in hexanes) to afford the product as a yellow solid (150. mg, 0.501 mmol, 63% yield). $^1$H NMR (500 MHz, CDCl$_3$) δ 6.45 (dd, J=8.4, 2.2 Hz, 2H), 6.39 (d, J=2.0 Hz, 2H), 6.26 (d, J=8.4 Hz, 2H), 5.32 (s, 1H), 2.25 (s, 6H). 13C NMR (125 MHz, CDCl$_3$) δ 169.76, 144.59, 142.94, 129.24, 116.25, 113.12, 109.88, 21.02. HRMS [M+H]$^+$ calculated mass for $C_{16}H_{14}NO_5$=300.0872, found=300.0879.

10-((5Z,8Z,11Z,14Z)-icosa-5,8,11,14-tetraenoyl)-10H-phenoxazine-3,7-diyl diacetate (2). A solution of 1 (61.2 mg, 0.204 mmol, 1.1 equiv) in anhydrous acetonitrile (1.2 mL) was treated sequentially with Na$_2$CO$_3$ (23.6 mg, 0.223 mmol, 1.2 equiv) and then arachidonoyl chloride (60.0 mg, 0.186 mmol, 1 equiv) in anhydrous acetonitrile (1 mL) at 0° C. The reaction was allowed to warm to room temperature before potassium iodide (83.3 mg, 0.502 mmol, 2.7 equiv) was added and the mixture was allowed to continue for 5 h under $N_2$ atmosphere in the dark. Once complete, the reaction was filtered, washed with EtOAc (3×), concentrated and purified by silica gel chromatography (eluent: 90% CH$_2$Cl$_2$ in hexanes) to obtain the product as an orange solid (53.3 mg, 0.091 mmol, 49% yield). $^1$H NMR (500 MHz, CDCl$_3$) δ 7.44 (d, J=8.7 Hz, 2H), 6.95-6.85 (m, 4H), 5.45-5.25 (m, 8H), 2.84-2.73 (m, 6H), 2.59 (t, J=7.4 Hz, 2H), 2.30 (s, 6H), 2.07 (dq, J=21.7, 7.3 Hz, 4H), 1.75 (q, J=7.4 Hz, 2H), 1.39-1.26 (m, 6H), 0.88 (t, J=6.8 Hz, 3H). $^{13}$C NMR (125 MHz, CDCl$_3$) δ 171.84, 168.98, 151.18, 148.79, 130.42, 128.93, 128.85, 128.49, 128.12, 128.09, 127.82, 127.49, 126.74, 125.42, 116.62, 110.80, 33.39, 31.46, 29.27, 27.16, 26.42, 25.58, 25.57, 25.53, 24.90, 22.52, 21.02, 14.03. HRMS [M+H]$^+$ calculated mass for $C_{36}H_{44}NO_6$=586.3169, found=586.3180.

CoxFluor. A solution of 2 (50. mg, 0.085 mmol, 1 equiv) in anhydrous MeOH (3 mL) was treated with Na (2 mg, 0.087 mmol, 1 equiv) at 0° C. and the reaction was allowed to continue at the same temperature for 0.5 h. When complete, the reaction was treated with aq. satd. NaHCO$_3$ and extracted with EtOAc (3×). The organic layer was dried over anhydrous sodium sulfate and purified by silica gel chromatography (eluent: 1% MeOH in CH$_2$Cl$_2$) to afford the product as an off-white solid (29.2 mg, 58.2 µmol, 68% yield). $^1$H NMR (500 MHz, CD$_3$OD) δ 7.88 (s, 2H), 7.28 (d, J=8.8 Hz, 2H), 6.59-6.55 (m, 4H), 5.39-5.24 (m, 8H), 2.80 (q, J=5.4 Hz, 4H), 2.74 (t, J=6.7 Hz, 2H), 2.60 (t, J=7.3 Hz, 2H), 2.04 (dt, J=11.7, 5.8 Hz, 4H), 1.66 (q, J=7.3 Hz, 2H), 1.38-1.29 (m, 6H), 0.88 (t, J=7.0 Hz, 3H). $^{13}$C NMR (125 MHz, CDCl$_3$) δ 173.29, 154.95, 151.90, 130.52, 128.96, 128.84, 128.55, 128.15, 127.87, 127.52, 125.64, 121.95, 110.44, 104.29, 33.36, 31.49, 29.69, 29.30, 27.20, 26.51, 25.62, 25.59, 25.55, 25.02, 22.56, 14.07. HRMS [M+H]$^+$ calculated mass for $C_{32}H_{40}NO_4$=502.2957, found=502.2943.

Arachidoyl Chloride. The material was prepared in an identical manner to arachidonoyl chloride according to a previously reported protocol (Soft Matter 2011, 7, 5319). Briefly, arachidic acid (50 mg, 0.160 mmol, 1.0 equiv) was dissolved in anhydrous CH$_2$Cl$_2$ (1 mL) and anhydrous DMF (30 µL) and placed under $N_2$ atmosphere. The solution was cooled to −5° C. in an ammonium chloride ice bath before oxalyl chloride (28 µL, 0.326 mmol, 2.0 equiv) in anhydrous CH$_2$Cl$_2$ (200 µL) was added. The reaction was maintained at the same temperature for 4 h and then allowed to sit at −20° C. overnight. The reaction was complete according to crude NMR and then it was concentrated. The residue was purified by dissolving in anhydrous hexanes, filtering, and re-concentrating the filtrate. The material was used without further purification.

10-icosanoyl-10H-phenoxazine-3,7-diyl diacetate (3). 1 (49.7 mg, 0.166 mmol, 1.1 equiv) in anhydrous acetonitrile (3 mL) was cooled to 0° C. and treated with Na$_2$CO$_3$ (19.2 mg, 0.181 mmol, 1.2 eq). A solution of arachidoyl chloride (50. mg, 0.151 mmol, 1 equiv) in anhydrous acetonitrile (3 mL) was added dropwise and allowed to warm to room temperature. Next, potassium iodide (124 mg, 0.747 mmol, 4.9 eq) was added and the mixture was allowed to stir at room temperature for 5 h under $N_2$ atmosphere in the dark. Once complete, the reaction was filtered, washed with EtOAc (3×), concentrated and purified by silica gel chromatography (eluent: 90% CH$_2$Cl$_2$ in hexanes) to obtain the product as a white solid (50.0 mg, 84.2 µmol, 55% yield). $^1$H NMR (500 MHz, CDCl$_3$) δ 7.45 (d, J=8.6 Hz, 2H), 6.94-6.85 (m, 4H), 2.57 (t, J=7.5 Hz, 2H), 2.30 (s, 6H), 1.64 (q, J=7.3 Hz, 2H), 1.24 (m, 32H), 0.88 (t, J=6.8 Hz, 3H). $^{13}$C NMR (125 MHz, CDCl$_3$) δ 172.20, 169.05, 151.24, 148.78, 126.87, 125.45, 116.65, 110.81, 34.06, 31.91, 29.69, 29.66, 29.63, 29.57, 29.42, 29.38, 29.35, 29.15, 25.30, 22.68, 21.06, 14.12. HRMS [M+H]$^+$ calculated mass for $C_{36}H_{52}NO_6$=594.3795, found=594.3806.

Scheme 3: Synthesis of Ctrl-CoxFluor

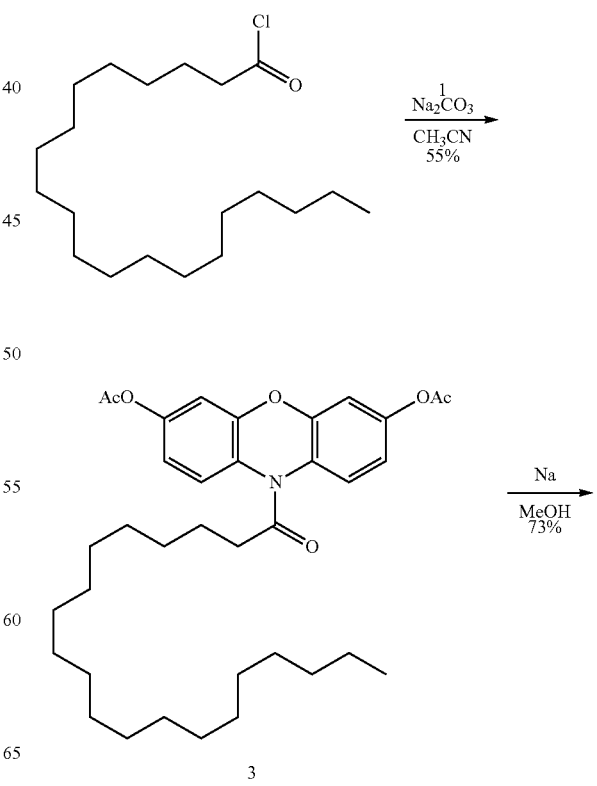

25

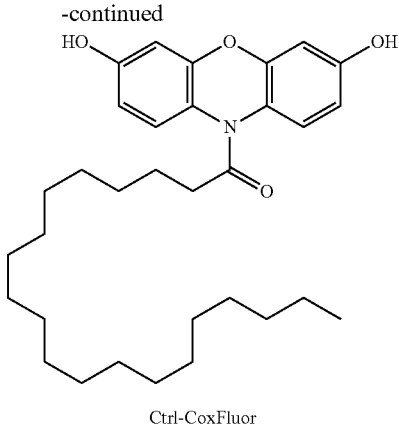

Ctrl-CoxFluor

Ctrl-CoxFluor. To a suspension of 3 (40. mg, 0.067 mmol, 1 eq) in dry MeOH (3 mL) at 0° C. was added Na (2 mg, 0.087 mmol, 1.3 equiv) and the reaction was stirred for 0.5 h. After completion, the reaction was treated with aq. satd. NaHCO$_3$ and extracted with EtOAc (3×). The organic layer was concentrated and purified by silica gel chromatography (eluent: 1% MeOH in CH$_2$Cl$_2$) to afford the product as a white solid (25 mg, 49 μmol, 73% yield). $^1$H NMR (500 MHz, CDCl$_3$) δ 7.17 (d, J=7.5 Hz, 2H), 6.58-6.43 (m, 4H), 2.47 (t, J=7.5 Hz, 2H), 1.53 (q, J=7.2, 6.7 Hz, 2H), 1.17 (d, J=13.3 Hz, 32H), 0.81 (t, J=6.9 Hz, 3H). $^{13}$C NMR (125 MHz, (CD$_3$)$_2$CO) δ 172.85, 157.04, 152.83, 126.86, 122.80, 110.85, 104.21, 34.34, 32.65, 30.40, 30.37, 30.22, 30.09, 29.84, 25.96, 23.34, 14.36. HRMS [M+H]$^+$ calculated mass for C$_{32}$H$_{48}$NO$_4$=510.3583, found=510.3583.

Scheme 4:
Synthesis of related heterocycles for fluorescent probes that can be made.

A.

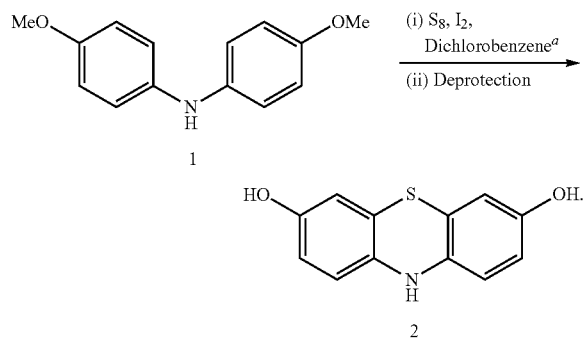

$^a$Nat. Chem. 2015, 7(9), 689-695

B.

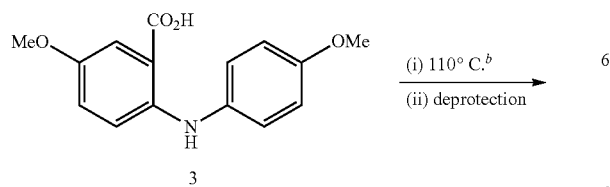

26

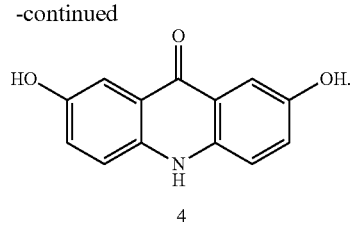

$^b$ J. Org. Chem. 2016, 81(16), 7244-7249

C.

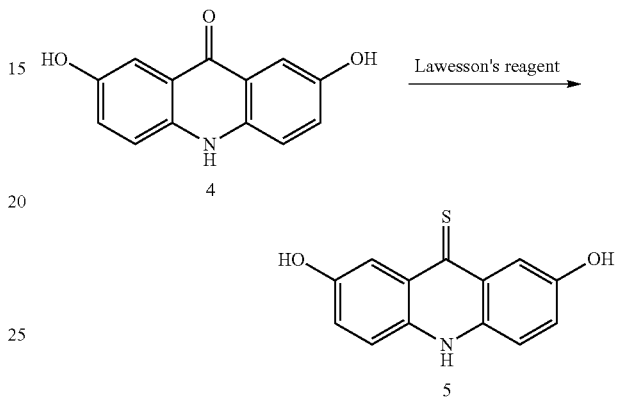

D.

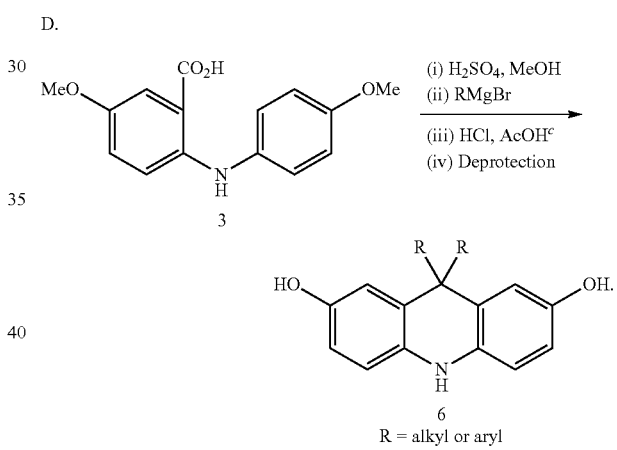

$^c$J. Mol. Struc. 2016, 1106, 399-406

E.

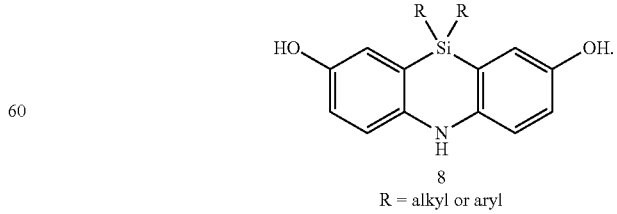

$^d$Angew. Chem. Int. Ed. 2003, 42(8), 921-924

-continued

F.

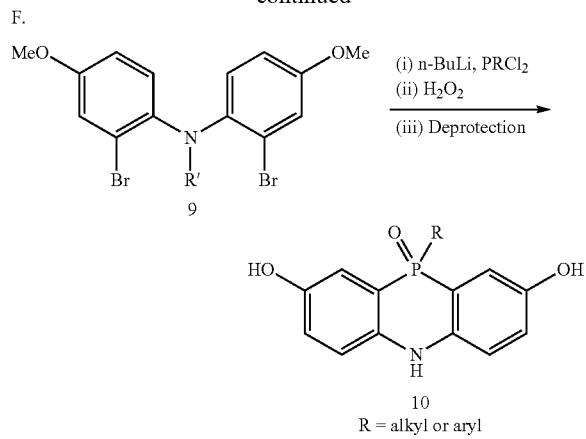

Example 3

General Methods for Assays and Characterization

Photophysical Characterization. Extinction coefficients and fluorescence quantum yields were acquired (n=3) and reported as the average with a relative standard deviation less than 15%. Extinction coefficients were acquired by titrating compound in 100 mM Tris-HCl (pH 8.0) within the linear range. Fluorescence quantum yields were obtained using the modified method for relative fluorescence quantum yield. Dye was titrated into the solution and the absorbance and emission were monitored (excitation at 540 nm). The absorbance was maintained below 0.1 to limit secondary absorbance events. Total emission spectra were integrated, and the relative quantum yield was calculated relative to Rhodamine B ($\phi$=0.70, ethanol). The refractive index of 100 mM Tris-HCl (pH 8.0) was measured to be 1.33514.

Fluorimeter Fluorescence Assay. The fluorescence assays were performed in microquartz cuvettes or submicroquartz cuvettes with a maximum volume of 600 µL. Reactions were monitored at room temperature using 540 nm excitation and emission was collected from 550-700 nm with a slit width of 1.25 mm. Total volumes of the reaction mixtures were maintained at 570 µL. To 100 mM Tris-HCl buffer (480 µL, pH 8.0) was added hemin (30 µL, 19 µM in 4% DMSO in 100 mM Tris-HCl, pH 8.0), COX-2 (30 µL, 4.75 µM 100 mM Tris-HCl, pH 8.0) and the reaction was initiated with CoxFluor (30 µL, 190 µM 10% DMSO in 100 mM Tris-HCl, pH 8.0). Final reaction concentrations were 1 µM hemin, 250 nM COX-2 and 10 µM CoxFluor in 100 mM Tris-HCl with 1.26% DMSO (v/v). Experiments in the presence of reduced GSH were conducted according to the same procedure, but GSH (30 µL, 19 mM in 100 mM Tris-HCl, pH 8.0) was added before the addition of CoxFluor for a final concentration of 1 mM. Assays performed in submicroquartz cuvettes were performed maintaining the same ratios, but with a final volume of 142.5 µL.

Plate Reader Fluorescence Assay. The fluorescence assays were performed at room temperature using 540 nm excitation and 590 nm emission. Total volume of the reaction mixture was maintained at 190 µL. To 100 mM Tris-HCl buffer (160 µL, pH 8.0) was added hemin (10 µL, 3.8 µM in 4% DMSO in 100 mM Tris-HCl, pH 8.0), COX-2 (10 µL, 950 nM in 100 mM Tris-HCl buffer, pH 8.0) and the reaction was initiated with CoxFluor (10 µL, 190 µM in 10% DMSO in 100 mM Tris-HCl, pH 8.0). Final reaction concentrations were 200 nM hemin, 50 nM COX-2 and 10 µM CoxFluor in 100 mM Tris-HCl with 1.26% DMSO (v/v). Inhibition assays were performed according to the same procedure, but COX-2 was preincubated with hemin and inhibitor for 0.5 h at 0° C. before initiation with CoxFluor. Relative fluorescence enhancement is calculated by comparing to a buffer control with 10 µM CoxFluor.

Enzyme Selectivity. Enzyme activity was defined as the amount substrate (µmol) consumed during one minute by one milligram of enzyme in 100 mM Tris-HCl at pH 8.0 under saturating conditions. Enzyme concentrations were measured using the BCA assay (Thermo Fisher Scientific) according to the published protocol with bovine serum albumin for the standard curve. COX-1 and COX-2 cyclooxygenase activities were measured using Strathkelvin oxygen electrode with arachidonic acid (200 µM). The oxygen electrode was calibrated using 1% sodium sulfite for 0% oxygen and atmosphere equilibrated 100 mM Tris-HCl at pH 8.0 for 100% oxygen. The reaction was monitored at 37° C. in a glass chamber with a total reaction volume of 1 mL. Hemin (5 µM), phenol (1 mM), and COX (2 µg) were added to atmosphere equilibrated buffer and then the reaction was initiated with AA (200 µM).

Porcine esterase activity was measured spectroscopically at 405 nm using p-nitrophenyl acetate (1.5 mM) as the substrate. Bovine catalase activity was measured using a discontinuous Amplex® Red-horseradish peroxidase assay to quantify the amount of hydrogen peroxide (initially 31.25 µM) remaining after 0.5 h incubation with excitation at 540 nm and emission at 590 nm. CYP2J2 activity was measured spectroscopically at 340 nm using cytochrome P reductase (3-fold excess), NADPH (1 mM), and arachidonic acid (70 µM) as the substrate. Rat liver microsome selectivity was performed at concentrations ranging from 12.5 µg/mL to 200 µg/mL and the largest turn-on was reported. Horseradish peroxidase activity was measured using hydrogen peroxide (31.25 µM) and Amplex® Red (50 µM) as the substrates with excitation at 540 nm and emission at 590 nm.

Myeloperoxidase selectivity was measured using the manufacturer's conditions (50 mM sodium acetate, pH 6.0, 100 mM NaCl) because the lysosomal enzyme is inactive at pH 8.0. Selectivity was assessed using 10-fold excess protein (350 µg/mL) and the solution was brought to a pH of 8.0 after 4 h with 0.5 M aq. NaOH prior to measurement. Monoamine oxidase A selectivity was assessed using human supersomes with 10-fold excess protein (350 µg/mL) under the standard COX conditions. 5-lipoxygenase selectivity was performed using the manufacturer's protocol and reported activity. Specifically, the active recombinant human protein in the insect cell lysate was diluted for a final activity of 1.01 U in 50 mM Tris-HCl buffer (pH 7.5) containing 2 mM CaCl$_2$, 1 mM ATP, and 4.6 µM 13(S)-HpODE. Prior to measuring the fluorescence, the solution was titrated with 0.5 M aq. NaOH for a pH 8.0.

When measured, all enzyme activities were confirmed to be under saturating conditions and within the first 20% of the reaction. The selectivity of CoxFluor (10 µM) was monitored after incubation with either 0.101 U COX-2 or 1.01 U of the other enzymes, unless noted otherwise above, in 100 mM Tris-HCl buffer at pH 8.0 using the plate reader with excitation at 540 nm and emission at 590 nm. Total reaction volume was maintained at 95 µL with a final DMSO concentration of 1.26% (v/v). Relative fluorescence enhancement is calculated by comparing to a buffer control containing 10 µM CoxFluor.

Analyte Selectivity. Response of CoxFluor (10 µM) to a variety of reactive oxygen, nitrogen, carbonyl, metals, and sulfur species (1, 3, 5, or 50 equiv) were monitored using the plate reader assay. Total volume of the reaction mixture was maintained at 190 μL in 100 mM Tris-HCl buffer (pH 8.0) with a final DMSO concentration of 1.26% (v/v). Assays for CoxFluor or resorufin were initiated by the addition of the analytes and the reactions were incubated at room temperature for up to 4 h. Measurements were recorded at a range of time points, and the relative turn-on was determined relative to a buffer control containing 10 μM CoxFluor or resorufin. Superoxide anion was added as a solution of potassium superoxide in DMSO. Nitroxyl was generated in situ from a solution of Angeli's salt in degassed 10 mM potassium hydroxide solution. Angeli's salt was prepared according to previously reported literature (Methods Enzymol. 1999, 301, 279). NO was generated in situ from a solution of MAHMA-NONOate in degassed 10 mM potassium hydroxide. Peroxynitrite was prepared according to previously reported literature (Anal. Biochem. 2006, 354, 165). All metals were prepared from their chloride salt. Formaldehyde solutions were prepared by depolymerizing saturated aqueous solutions at 100° C. before use. Dehydroascorbic acid was prepared by dissolving the solid at 65° C. in water before cooling to room temperature for use. All other analytes were prepared by dilution or dissolution from commercially available sources.

CoxFluor, Ctrl-CoxFluor & Resorufin Stability Assays. Stability assays were performed for a 10 μM solution of each compound in a series of buffers/solvents (100 mM Tris-HCl at pH 8.0, DMEM with 10% FBS, DMEM without serum and DMSO). Stability was assessed at room temperature or at 37° C. and in the presence or absence of ambient light. Fluorescence was measured using the plate reader with excitation at 540 nm and emission from 560-700 nm and the relative turn-on was determined by the change of fluorescence intensity at 590 nm.

Example 4

Cellular Assays

Cell Culture. HEK 293T and RAW 264.7 macrophage cells were acquired from ATCC and Prof. Elvira de Mejia (Food Science and Human Nutrition, UIUC), respectively. Cells were cultured in phenol-red free Dulbecco's modified eagle medium (DMEM, Corning) supplemented with 10% fetal bovine serum (FBS, Sigma Aldrich), and 1% penicillin/streptomycin (Corning). Incubation with 0.25% trypsin containing EDTA and phenol red (Gibco™, Fisher Scientific) or manual scrapping is used for passaging for HEK 293T and RAW 264.7 macrophage cells, respectively. Cells were incubated at 37° C. with 5% $CO_2$. Experiments were performed in 4-well chambered cover glasses (Lab-Tek, Thermo Scientific), 96-well plates (Nunc, Thermo Scientific), or 6-well plates (BioLite, Thermo Scientific).

Trypan Blue Exclusion Cytotoxicity Assay. 6-well plates were seeded with 300,000 cells per well (2 mL of 150,000 cells/mL) and incubated at 37° C. with 5% $CO_2$ for 48 to 72 h (~60-80% confluent). Media was removed and replaced with either 5, 10, or 25 μM CoxFluor in fresh serum-free DMEM media (1.25% DMSO v/v final concentration). After 6 h the media was removed, and cells were trypsinized with 200 μL 0.25% trypsin-EDTA for less than 5 minutes at 37° C. The trypsin was quenched with the addition of 1.8 mL DMEM media containing 10% FBS and the cells were mixed thoroughly before diluting 1:1 with trypan blue (0.4% in PBS w/v). Percent viability was measured using a Countess® II FL Automated Cell Counter (Thermo Fisher Scientific), where the parameters were optimized to identify live and dead cells. Viability was calculated by the relative to the vehicle control.

MTT Cytotoxicity Assay. 96-well plates were seeded with 20,000 cells per well (200 μL of 100,000 cells/mL, RAW 264.7 macrophage) or 25,000 cells per well (200 μL of 125,000 cells/mL, HEK 293T cells) and incubated at 37° C. with 5% $CO_2$ for 72 h (~90% confluent). Media was removed and fresh serum-free DMEM media containing 0, 5, 10, or 25 μM CoxFluor (1.25% DMSO final v/v) was added. The media was removed at various time points (3 or 6 h) and replaced with 200 μL 20:1 mixture of FBS-free DMEM and (3-(4,5-dimethylthiazol-2-yl)-2,5-diphenyl-tetrazolium bromide (MTT, 5 mg/mL stock in PBS). The cells were incubated for 4 h under the same conditions and then the medium was removed and replaced with DMSO (200 μL/well). The absorbance of each well was recorded after a 1:5 dilution in DMSO at 555 nm on a microplate reader. Viability was calculated by the absorbance relative to the vehicle control.

HEK293T Transfection with Human COX-2. The plasmid containing human COX-2 (pcDNA3.1-hPTGS2-2flag) was purchased from Addgene (Catalog #102498). The plasmid was isolated from a single colony that was grown to turbidity overnight at 37° C. in Luria broth (LB) media with 100 μg/mL ampicillin (5 mL) using the GeneJET plasmid Miniprep (Thermo Scientific) according to the manufacturer's protocol (the plasmid was eluted with Milli-Q water rather than the elution buffer). Plasmid concentration was determined using the absorbance at 260 nm on a NanoDrop 2000 spectrometer. Prior to plating onto 4-well chambered cover glasses, the surface exposed substrate was coated with R&D Systems™ Cultrex Poly-L-Lysine (Fisher Scientific) according to the manufacturers protocol (allowed to dry>3 h). Plates were seeded with 175,000 cells per well (500 μL of 350,000 cells/mL in DMEM media supplemented with 10% FBS) and allowed the cells to incubate for 40 h at 37° C. with 5% $CO_2$ (60-70% confluent). Transfections was performed using Lipofectamine 3000 (Thermo Fisher Scientific) according to the manufacturer's protocol. Briefly, 180 μL of transfection master mix was prepared by a 1:1 dilution of lipofectamine 3000 reagent (5.4 μL in 90 μL Opti-MEM™ Reduced Serum Media) and DNA complexed to P3000 reagent (1,800 ng plasmid with 3.6 μL P3000 in Opti-MEM™ Reduced Serum Media) and the master mix was allowed to incubate at room temperature for 5 to 10 minutes. Media was removed from each well and replaced with 500 μL Opti-MEM™ Reduced Serum Media followed by the addition of 20 μL transfection master mix. After 48 h incubation at 37° C. with 5% $CO_2$ (~90-100% confluent) the cells were subjected to experimental conditions for imaging.

Confocal Fluorescence Live-Cell Imaging of Human COX-2 Transfected HEK 293T cells. Transfections were performed using the Lipofectamine 3000 reagent according to the aforementioned protocol. Control wells were treated the same as the transfected wells without the addition of the transfection master mix. The media was removed from each well and replaced with serum-free DMEM media containing 10 μM CoxFluor or 10 μM CoxFluor with 10 μM indomethacin (1% DMSO final concentration). Cells were incubated at 37° C. with 5% $CO_2$ before imaging with excitation at 555 nm and emission collected from 565-700 nm. Each well was imaged using a Zeiss LSM 700 confocal microscope (n=3 technical replicates; n=4 biological replicates). For GSH knockdown experiments, the initial media change was performed with 1 mM NEM (0.1% DMSO final concentration) in serum-free DMEM media and the cells were allowed to incubate for 30 minutes before proceeding to the staining with CoxFluor. Images were quantified over the entire imaging window, without any processing, using ImageJ (v. 1.51, NIH). All images were processed using identical parameters and false colored (LUT: jet.lut) in ImageJ.

RAW 264.7 Macrophage Activity Assays. 6-well plates were seeded with 250,000 cells per well (2.0 mL of 125,000 cells/mL) and the cells were allowed to incubate at 37° C. with 5% $CO_2$ for 72 h (~70-80% confluent). The media was removed and replaced with serum-free DMEM (1.98 mL). Lipopolysaccharide was added in PBS (20 µL 100 µg/mL for final concentration of 1 µg/mL) at 2, 4, 6, 8, 10, 19, and 24 h (n=3 biological replicates) prior to lysis. Control wells were prepared by adding PBS without LPS at the 24 h time point. The media was removed, and the cells were lysed by adding CelLytic M (200 µL, Millipore-Sigma) and mixing for 15 minutes at room temperature. The solution was mixed well via pipette followed by vortex for 10 seconds. Cellular debris was removed by centrifugation using a Fisher Scientific accuSpin Micro 17R centrifuge at 6,000 rpm for 10 minutes (4° C.). The samples were stored at 4° C. and activity was measured immediately. Activity was measured according to a modified fluorimeter assay with excitation at 540 nm, emission at 590 nm, and slit width of 0.8 mm. Specifically, to a solution of 888 µL 100 mM Tris-HCl buffer (pH 8.0) and 100 µL lysate was added 10 µL 100 mM N-ethylmaleimide (1 mM final concentration) and the solution was allowed to incubate at room temperature for 1 minute. The reaction was initiated with 2 µL 2 mM CoxFluor (4 µM final concentration, 1.2% DMSO final) and the kinetics were monitored over 2 minutes. Rates were measured within the linear region (usually the first 30 seconds after initiating the reaction). A calibration curve was constructed with resorufin in buffer containing 1 mM N-ethylmaleimide, 10% CelLytic M, and a final DMSO concentration of 1.2%. Total protein concentration was measured using the BCA assay (Thermo Fisher Scientific) to calculate COX-2's specific activity.

Confocal Fluorescence Live-Cell Imaging of Lipopolysaccharide-activated RAW 264.7 Macrophages. The surface exposed substrate of 4-well chambered cover glasses was coated with R&D Systems™ Cultrex Poly-L-Lysine (Fisher Scientific) using the manufacturer's protocol. Plates were seeded with 180,000 cells per well (500 µL of 360,000 cells/mL in DMEM media supplemented with 10% FBS) and were allowed to incubate for 38 h at 37° C. with 5% $CO_2$ (70-80% confluent). The media was removed and replaced with serum-free DMEM media containing 0.2 mM BSO and either PBS or 1 µg/mL lipopolysaccharide in PBS (500 µL final volume). The cells were incubated under these conditions for 17 h at 37° C. with 5% $CO_2$. Next, the media was replaced with the same conditions with or without indomethacin (10 µM) for 2 h at 37° C. with 5% $CO_2$ (500 µL final volume containing 0.2% DMSO final concentration). Finally, the cells were stained under identical conditions supplemented with 10 µM CoxFluor (500 µL final volume containing 1.5% DMSO final concentration). After incubation at 37° C. with 5% $CO_2$ for 4 h, each well was imaged using a Zeiss LSM 700 confocal microscope (n=3 technical replicates; n=4 biological replicates). Images were quantified over the entire imaging window, without any processing, using ImageJ (v. 1.51, NIH). All images were processed using identical parameters and false colored (LUT: jet.lut) in ImageJ.

Flow Cytometry of Lipopolysaccharide-induced COX-2 Expression in RAW 264.7 Macrophages. RAW 264.7 macrophage cells (300,000 cells, 2 mL of 150,000 cells/mL) were seeded into 6-well plates and incubated for 48 to 72 h under standard conditions for a final confluency of ~60-80%. The media was removed and replaced with serum-free DMEM (1.98 mL) followed by LPS (1 µg/mL final concentration, 20 µL of 100 µ/mL in PBS) at 4 or 19 h before collection. Cellular GSH was depleted 2 h prior to collection via treatment with BSO (0.2 mM final concentration, 40 µL 10 mM solution in 1:1 DMSO: serum-free DMEM, 1% DMSO final concentration). Cells were collected by treatment with 0.5 mL 0.25% trypsin-EDTA for less than 5 minutes at 37° C. and then the trypsin was inactivated with 1.0 mL DMEM media containing 10% FBS. The solution was partitioned for two samples, which were subsequently collected via centrifugation at 6,000 RPM at 4° C. in 1.6 mL Eppendorf tubes. The media was removed, and cells were resuspended in 0.2 mM BSO either with or without 10 µM CoxFluor (1 mL, 1.5% DMSO final concentration in serum-free DMEM) for 90 minutes at 37° C. with agitation. When performing inhibition studies, the aforementioned staining solutions were prepared with 20 µM indomethacin without affecting the final concentration of DMSO. After staining, cells were pelleted using the aforementioned procedure and were resuspended in PBS. Samples were stored on ice prior to analysis on a BD LSR Fortessa Flow Cytometry Analyzer with 561 nm excitation and 582/15 emission bandpass filter. Dead cells were excluded from the analysis by staining samples (~300 µL) with propidium iodide (1 µL of 1 mg/mL in deionized water) for 5 to 10 minutes at room temperature before analysis with 561 nm excitation and 595 nm longpass dichromic mirror and 610/20 emission bandpass filter. Data was gated for cells according to side and forward scatter areas, live cells using the forward scatter area versus PE-Texas Red area, and for single cell events using the forward scatter width versus side scatter area. Replicate numbers correspond to biological replicates.

Flow Cytometry Measurement of COX-2 Activity in RAW 264.7 Macrophages under AneroPack® Hypoxic Conditions. RAW 264.7 macrophage cells (300,000 cells, 2 mL of 150,000 cells/mL) were seeded into 6-well plates and incubated for 48 to 72 h under standard conditions for a final confluency of ~60-80%. The media was removed and replaced with serum-free DMEM (1.98 mL) followed by LPS (1 µg/mL final concentration, 20 µL of 100 µg/mL in PBS) 19 h before collection. Cellular GSH was depleted 2 h prior to collection via treatment with BSO (0.2 mM final concentration, 40 µL 10 mM solution in 1:1 DMSO: serum-free DMEM, 1% DMSO final concentration). Cells were collected by treatment with 0.5 mL 0.25% trypsin-EDTA for less than 5 minutes at 37° C. and then the trypsin was inactivated with 1.0 mL DMEM media containing 10% FBS. The solution was partitioned for two samples, which were subsequently collected via centrifugation at 6,000 RPM at 4° C. in 1.6 mL Eppendorf tubes. The media was removed, and cells were resuspended in 0.2 mM BSO with 10 µM CoxFluor (1.0 mL 1.5% DMSO final concentration in degassed serum-free DMEM) and incubated for 90 minutes at 37° C. in a sealed container either with or without an AneroPack® (Mitsubishi Gas Company).

When performing inhibition studies, the aforementioned staining solutions were prepared with 20 µM indomethacin without affecting the final concentration of DMSO. After staining, cells were pelleted in 1.6 mL Eppendorf tubes using the aforementioned procedure and were resuspended in degassed PBS. Samples were stored on ice prior to analysis on a BD LSR Fortessa Flow Cytometry Analyzer with 561 nm excitation and 582/15 emission bandpass filter.

Dead cells were excluded from the analysis by staining samples (~300 μL) with propidium iodide (1 μL of 1 mg/mL in deionized water) for 5 to 10 minutes at room temperature before analysis with 561 nm excitation and 595 nm longpass dichromic mirror and 610/20 emission bandpass filter. Data was gated for live cells the forward scatter higher versus PE-Texas Red area, and for single cell events using the forward scatter width versus side scatter area. Replicate numbers correspond to biological replicates.

Flow Cytometry Measurement of COX-2 Activity in RAW 264.7 Macrophages under Variable Oxygen Concentrations. RAW 264.7 macrophage cells (500,000 cells, 2 mL of 250,000 cells/mL) were seeded into 6-well plates and incubated for 48 h under standard conditions for a final confluency of ~80%. The media was removed and replaced with serum-free DMEM (1.98 mL) followed by LPS (1 μg/mL final concentration, 20 μL of 100 μg/mL in PBS) 19 h before collection. Cellular GSH was depleted 2 h prior to collection via treatment with BSO (0.2 mM final concentration, 40 μL 10 mM solution in 1:1 DMSO: serum-free DMEM, 1% DMSO final concentration). Cells were collected by treatment with 0.5 mL 0.25% trypsin-EDTA for less than 5 minutes at 37° C. and then the trypsin was inactivated with 1.0 mL DMEM media containing 10% FBS. Three wells were pooled (1.5 mL×3) for a final volume of 4.5 mL cell suspension before partitioning into three tubes (one tube per oxygen concentration) for centrifugation at 6,000 RPM at 4° C. in 1.6 mL Eppendorf tubes. The media was removed, and cells were resuspended in 0.2 mM BSO with 10 μM CoxFluor (1.5 mL, 1.5% DMSO final concentration in pre-equilibrated serum-free DMEM; media was equilibrated for ~24 h at the desired oxygen concentration followed by ~2 h re-equilibration following the addition of BSO; CoxFluor was added immediately before use prevent any photo-oxidation).

The resulting cell suspension was incubated for 90 minutes at 37° C. under ~21, 1.0, or 0.1% oxygen with 5% $CO_2$ in an ultra-low cell attachment six well plate (Corning® Costar®) to facilitate rapid oxygen exchange. After staining, cells were pelleted using the aforementioned procedure and were resuspended in PBS. Samples were stored on ice prior to analysis on a BD LSR Fortessa Flow Cytometry Analyzer with 561 nm excitation and 582/15 emission bandpass filter. Dead cells were excluded from the analysis by staining samples (~300 μL) with propidium iodide (1 μL of 1 mg/mL in deionized water) for 5 to 10 minutes at room temperature before analysis with 561 nm excitation and 595 nm longpass dichromic mirror and 610/20 emission bandpass filter. Data was gated for live cells the forward scatter higher versus PE-Texas Red area, and for single cell events using the forward scatter width versus side scatter area. Replicate numbers correspond to biological replicates.

Enzyme-Linked Immunosorbent Assay (ELISA) for Mouse COX-2. Protein concentration was measured directly from the same samples as the Flow Cytometry Measurement of COX-2 Activity in RAW 264.7 Macrophages under Variable Oxygen Conditions. The ELISA was performed using the SimpleStep ELISA Mouse COX2 ELISA Kit (ab210574, Abcam) according to the manufacturer's protocol. Briefly, cells were washed with cold PBS (1.0 mL×2) and then lysed in cold 1× Cell Extraction Buffer PTR for 20 minutes at 0° C. The debris was removed via centrifugation at 18,000×g for 20 minutes at 4° C. and the supernatants were collected and stored at −80° C. prior to use. Protein concentration was measured using the BCA Assay (Thermo Fisher Scientific) according to the manufacturer's protocol and the lysate was diluted with 1× Cell Extraction Buffer PTR for a final concentration of 25 μg/mL total protein. Cell lysate (50 μL) and then Antibody Cocktail (50 μL) were added to each well in duplicate and the sealed plate was incubated with vigorous shaking (400 rpm) for 1 h at 22° C. After binding, each well was washed thoroughly with 1× Wash Buffer PT (350 μL×3). TMB Substrate (100 μL) was added to each well and allowed to incubate in the dark with vigorous stirring for 10 minutes at 22° C. before quenching with Stop Solution (100 μL). The optical density was measured at 450 nm and the protein concentration was interpolated according to a standard curved (prepared in duplicate). Protein concentrations are reported for the COX-2 concentration in a 25 μg/mL total protein stock.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula II:

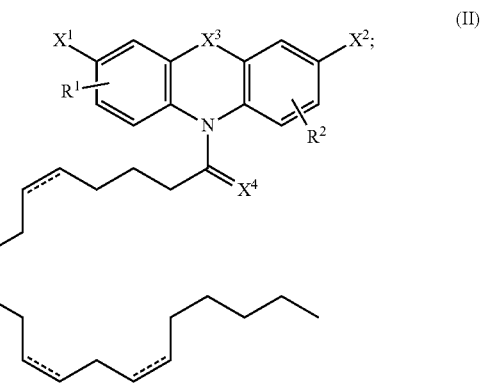

wherein
each ------- is independently a double bond or a single bond;
$R^1$ and $R^2$ are independently H, halo, amino, nitro, cyano, or —$(C_1$-$C_6)$alkyl;
$X^1$ and $X^2$ are independently OH, SH, or OC(=O)($C_1$-$C_6$)alkyl;
$X^3$ is O, S, $SiR_2$, $SiPh_2$, $CR_2$, $CPh_2$, C(fluorene), C(=O), C(=S), P(=O)R, or P(=O)OR wherein R is —$(C_1$-$C_6)$alkyl; and
$X^4$ is O or S.

2. The compound of claim 1 wherein each ------- is a double bond.

3. The compound of claim 1 wherein each ------- is a single bond.

4. The compound of claim 1 wherein $X^1$ and $X^2$ are OH, and $X^3$ and $X^4$ are O.

5. The compound of claim 1 wherein $R^1$ and $R^2$ are H.

6. A compound of Formula III:

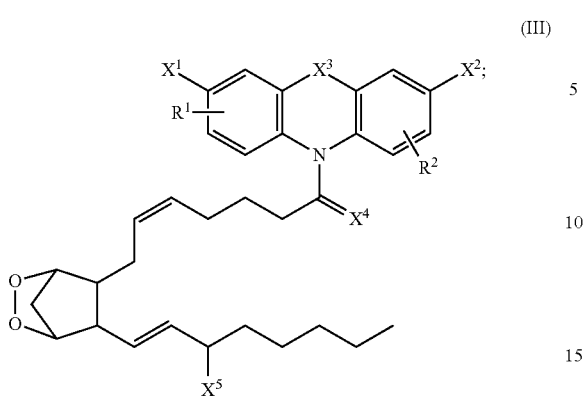

wherein
$R^1$ and $R^2$ are independently H, halo, amino, nitro, cyano, or —$(C_1-C_6)$alkyl;
$X^1$ and $X^2$ are independently OH, SH, or OC(=O)$(C_1-C_6)$alkyl;
$X^3$ is O, S, SiR$_2$, SiPhs, CR$_2$, CPh$_2$, C(fluorene), C(=O), C(=S), P(=O)R, or P(=O)OR wherein R is —$(C_1-C_6)$alkyl;
$X^4$ is O or S; and
$X^5$ is OH, SH, or OOH.

7. The compound of claim 6 wherein $X^4$ is O.

8. The compound of claim 6 wherein the compound is:

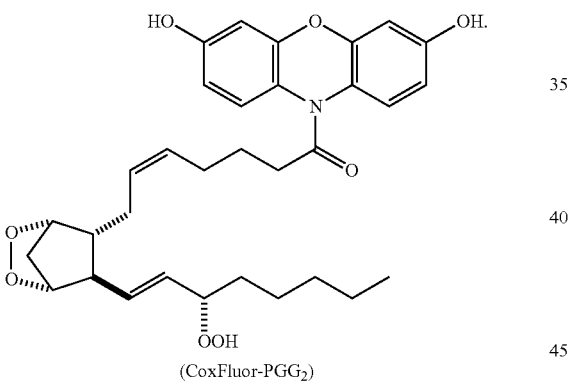

(CoxFluor-PGG$_2$)

9. The compound of claim 1 wherein the compound is:

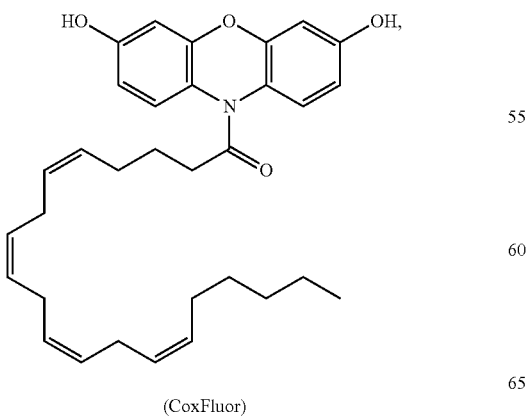

(CoxFluor)

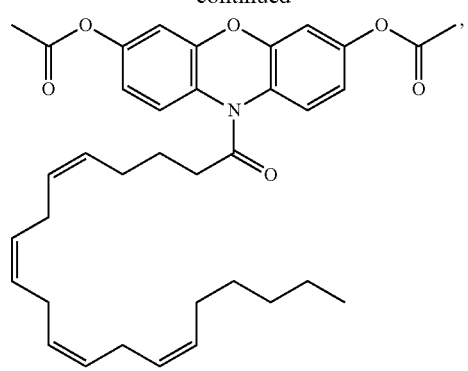

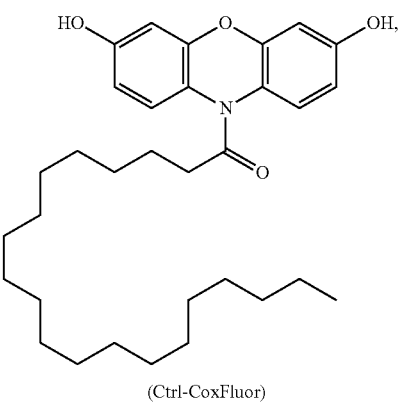

(Ctrl-CoxFluor)

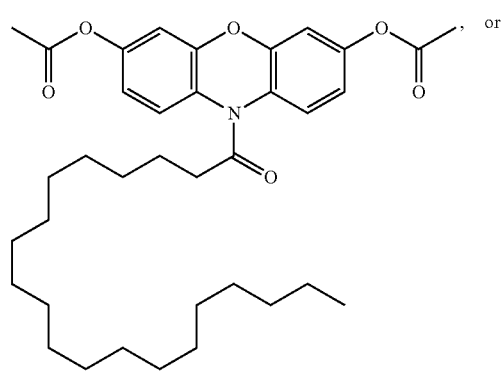

, or

10. The compound of claim 9 wherein the compound is CoxFluor.

11. A method for imaging cyclooxygenase-2 (COX-2) activity in a cell comprising:

a) contacting a cell and a compound of Formula IIB:

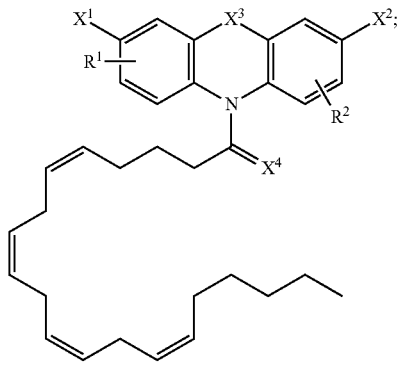

(IIB)

wherein $R^1$ and $R^2$ are independently H, halo, amino, nitro, cyano, or —($C_1$-$C_6$)alkyl;

$X^1$ and $X^2$ are independently OH, SH, or OC(=O)($C_1$-$C_6$)alkyl;

$X^3$ is O, S, $SiR_2$, $SiPh_2$, $CR_2$, $CPh_2$, C(fluorene), C(=O), C(=S), P(=O)R, or P(=O)OR wherein R is —($C_1$-$C_6$)alkyl; and $X^4$ is O or S;

wherein the contacting hydrolyzes the amide bond of a compound of Formula IIB to release from it a fluorescent compound having a fluorescent intensity; and b) quantifying the fluorescent intensity of the fluorescent compound by comparing the fluorescent intensity of the fluorescent compound to a control;

thereby imaging the COX-2 activity of the cell.

12. The method of claim 11 wherein the cell comprises COX-2.

13. The method of claim 11 wherein the fluorescent compound is resorufin.

14. The method of claim 11 wherein the cell is further contacted with a cyclooxygenase inhibitor at step a).

15. The method of claim 14 wherein the cyclooxygenase inhibitor is indomethacin, celecoxib, or a celecoxib analog.

16. The method of claim 11 wherein quantifying the fluorescent intensity is performed by flow cytometry.

* * * * *